United States Patent
Suh et al.

(10) Patent No.: US 9,650,638 B2
(45) Date of Patent: May 16, 2017

(54) APTAMER FOR PERIOSTIN AND ANTI-CANCER COMPOSITION INCLUDING SAME

(71) Applicants: UNIST ACADEMY-INDUSTRY RESEARCH CORPORATION, Ulsan (KR); POSTECH ACADEMY-INDUSTRY FOUNDATION, Pohang (KR)

(72) Inventors: Pann-Ghill Suh, Ulsan (KR); Ii Shin Kim, Ulsan (KR); Yu Jin Lee, Busan (KR); Youn Dong Kim, Pohang (KR); Young Chan Chae, Pohang (KR); Jong Hun Im, Pohang (KR); Sung Ho Ryu, Pohang (KR)

(73) Assignees: UNIST (ULSAN NATIONAL INSTITUTE OF SCIENCE AND TECHNOLOGY), Ulsan (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 27 days.

(21) Appl. No.: 14/411,176

(22) PCT Filed: Nov. 12, 2012

(86) PCT No.: PCT/KR2012/009521
§ 371 (c)(1),
(2) Date: Dec. 24, 2014

(87) PCT Pub. No.: WO2014/007438
PCT Pub. Date: Jan. 9, 2014

(65) Prior Publication Data
US 2015/0337309 A1    Nov. 26, 2015

(30) Foreign Application Priority Data

Jul. 2, 2012   (KR) .................. 10-2012-0071664
Nov. 12, 2012  (KR) .................. 10-2012-0127287

(51) Int. Cl.
*A61K 48/00*    (2006.01)
*C12N 15/11*    (2006.01)
(Continued)

(52) U.S. Cl.
CPC ........ *C12N 15/115* (2013.01); *A61K 31/7088* (2013.01); *G01N 33/57492* (2013.01);
(Continued)

(58) Field of Classification Search
USPC .......................................... 536/24.5; 514/44
See application file for complete search history.

(56) References Cited

U.S. PATENT DOCUMENTS 8,017,119 B2    9/2011  Taniyama et al.
2011/0033875 A1  2/2011  Pierce et al.
(Continued)

FOREIGN PATENT DOCUMENTS

| CN | 101809167 | 8/2010 |
| WO | 2009-012418 | 1/2009 |
| WO | 2011-130195 | 10/2011 |

OTHER PUBLICATIONS

Laura Morra et al., "Periostin expression and epithelian-mesenchymal transition in cancer: a review and an update", Virchows Arch, Oct. 14, 2011, vol. 459, No. 5, pp. 465-475.
(Continued)

*Primary Examiner* — Terra C Gibbs
(74) *Attorney, Agent, or Firm* — Lex IP Meister, PLLC

(57) ABSTRACT

This disclosure relates to DNA aptamer specifically binding to periostin, which is cancer-related protein, a composition for inhibiting cancer and/or cancer metastasis and/or a composition for diagnosis of cancer and/or cancer metastasis, comprising the same as an active ingredient, wherein the
(Continued)

aptamer has different binding mechanism from the existing antibodies, and thus, may inhibit and diagnose cancer/cancer metastasis more effectively.

12 Claims, 15 Drawing Sheets

(51) Int. Cl.
    *C07H 21/02*      (2006.01)
    *C07H 21/04*      (2006.01)
    *C12N 15/115*      (2010.01)
    *G01N 33/574*      (2006.01)
    *A61K 31/7088*      (2006.01)

(52) U.S. Cl.
    CPC .... *C12N 2310/16* (2013.01); *C12N 2310/335* (2013.01); *C12N 2320/30* (2013.01); *G01N 2333/705* (2013.01)

(56) References Cited

U.S. PATENT DOCUMENTS

2011/0104166 A1    5/2011    Stankovic et al.
2011/0177613 A1    7/2011    Adler et al.

OTHER PUBLICATIONS

Jonathan D, Vaught et al., "Expanding the Chemistry of DNA for in Vitro Selection", JSCS Articles, vol. 132, No. 12, pp. 4141-4151, Mar. 31, 2010.

Search Report, EPO, EP Patent Application No. 12880412.7, Feb. 16, 2016.

International Search Report dated Mar. 29, 2013 of the PCT application No. PCT/KR2012/009521.

Lee, Y. J. et al, "DNA aptamer-targeted periostin inhibit adhesion and migration of breast cancer cells," Proceedings of the 10th JBS Biofrontier Symposium commemorating Kyushu University Centennial Anniversary, pp. 70 (Nov. 14-16, 2011).

Lee, Y. J. et al, "DNA aptamer-targeted periostin inhibits adhesion and migration of breast cancer," Proceedings of AACR 103rd Annual Meeting 2012, abstract 5190, (Apr. 4, 2012).

Kyutoku, M. et al, "Role of periostin in cancer progression and metastasis: inhibition of breast cancer progression and metastasis by anti-periostin antibody in a murine model," International Journal of Molecular Medicine, Aug. 2011, vol. 28(2), pp. 181-186.

Lee, Y. J. et al., "Periostin-binding DNA aptamer inhibits breast cancer growth and metastasis," Molecular Therapy, online publication Mar. 19, 2013; doi: 10.1038/mt. 2013.30.

Y. Kudo et al. "Periostin: Novel diagnostic and therapeutic target for cancer", Histol. Histopathol. 22(10): 1167-1174, Oct. 2007.

Edward N. Brody et al. "Aptamers as therapeutic and diagnostic agents", J. Biotechnol. 74(1): 5-13, Mar. 2013.

APTAMER FOR PERIOSTIN AND ANTI-CANCER COMPOSITION INCLUDING SAME

TECHNICAL FIELD

The present invention relates to DNA aptamer specifically binding to periostin, which is cancer-related protein, a composition for inhibiting cancer and/or cancer metastasis and/or a composition for diagnosis of cancer and/or cancer metastasis, comprising the same as an active ingredient.

BACKGROUND OF THE INVENTION

The progression of solid cancer to invasive tumor is the major prerequisite in metastasis, and involves changes in cell morphology and motility and the like. Although genetic modification in cancer cells is varied according to the type of metastatic cancer, it causes common result of cancer cells being separated from its originating organ and dispersed in various organs. Under such tumor microenvironment, various growth factors, angiogenesis factors, and proteases are secreted by cancer cells and cancer associated cells, and they induce cancer growth and angiogenesis and decompose extracellular matrix to promote cancer cell invasion and metastasis. In addition, osteopontin (OPN), tenascin C, and matricellular proteins contribute to tumor metastasis, and regulate the maintenance and expansion of normal or tumor stem cells and metastatic niches. As an alternative to targeting a specific stage of cancer progression, it can be considered to select a molecule performing an important function in a plurality of stages of cancer development and target it. Among these molecules, periostin is considered as an important protein regulating cell adhesion and interaction of cells and matrix.

Periostin is one of extracellular matrix proteins, and it is secretory protein that is involved in cell adhesion, acts as cytokine and transduces signals through cell adhesion molecules integrin $\alpha v\beta_3$ and $\alpha v\beta_5$. At first, it is discovered as osteoblast specific factor, and is highly expressed in periosteum of bone tissue. Since periostin is overexpressed in various epithelial carcinoma such as breast cancer, and the function is related to the critical stages of malignant process such as metastasis and angiogenesis, recently, there is a rising interest in periostin. Although periostin is not expressed in normal breast cell line, the expression is specially increased in the case of breast cancer. And, periostin is an important limiting factor during metastatic colonization, promotion of cell survival, angiogenesis and the maintenance of tumor stem cells. Many clinical studies show that the overexpression of periosin and increase in serum concentration of periostin are related to metastatic tumor growth and bad prognosis. In addition, periostin is an important limiting factor that promotes cell survival, angiogenesis and the maintenance of tumor stem cells during metastatic colonization. Thus, periostin was confirmed as a promising candidate substance related to the inhibition of tumor growth and metastasis.

Biologically targeted therapy has been a main stream of cancer treatment for last 20 years. Compared to the existing therapy exhibiting toxicity even to normal cells, targeted therapy receives attention as more effective therapy because it is more specific and has low toxicity to normal cells. Nucleic acid-based aptamers are on the rise as targeted therapeutic molecules. Aptamer is a single strand DNA or RNA, and very closely and specifically binds to a target molecule. Aptamer is developed by a repeated selection method named SELEX (Systematic evolution of ligands by exponential enrichment), and it selectively recognizes its target and binds thereto using a specific three-dimensional structure. Aptamer can regulate the function of a protein target by directly binding to the target. Due to the nature of short nucleic acid, aptamer has advantages in terms of improved stability, convenience in production and modification, low immunogenicity and low toxicity and the like, compared to other therapeutic means. Thus, the value of aptamer is being recognized as an alternative to low molecule and antibody-based therapy.

Accordingly, there is a demand for development of periostin on the rise as a promising anticancer target, aptamer specifically binding thereto, and anticancer therapeutic technology using the same.

DISCLOSURE

Technical Problem

Therefore, one embodiment of the invention provides periostin aptamer that specifically binds to periostin, and comprises modified bases that are substituted with a hydrophobic functional group selected from the group consisting of a naphthyl group, a benzyl group, a pyrrole benzyl group, and tryptophan at 5-position of dU (deoxyuracil).

Another embodiment provides a pharmaceutical composition for treating cancer comprising the periostin aptamer as an active ingredient, a method for treating cancer comprising the step of administering a pharmaceutically effective amount of the periostin aptamer to a patient in need of treatment of cancer, and use of the periostin aptamer for treatment of cancer.

Still another embodiment provides a composition for diagnosis of cancer comprising the periostin aptamer as an active ingredient, and use of the periostin aptamer for diagnosis of cancer.

Still another embodiment provides a method for providing information on the diagnosis of cancer using the periostin aptamer.

Technical Solution

The inventors developed modified DNA-aptamer named as PNDA-3, which can bind to periostin secreted from cancer cells with high affinity, and completed the invention. It was also confirmed that PDNA-3 blocks interactions between integrin ($\alpha_v\beta_3$ and $\alpha_v\beta_5$) and periostin, and inhibits biological functions of periostin. The data provided herein shows that PNDA-3 binding to periostin inhibits adhesion, migration and invasion capability in breast cancer cell, reduces the activation of integrin $\alpha v\beta_3$- and $\alpha v\beta_5$-dependent signal transduction pathway, and blocks the interaction of receptors on cell surface. It was also confirmed that the administration of PNDA-3 decreases breast cancer growth, metastasis and angiogenesis in a breast cancer metastasis mouse model. Thus, the aptamer of the present invention is useful as anticancer substance for inhibiting the growth and/or metastasis of solid cancer such as breast cancer.

It is an object of the invention to provide periostin aptamer that highly specifically binds to periostin protein related to cancer development and metastasis, thereby inhibiting cancer and/or cancer metastasis or enabling diagnosis of cancer, and inhibitors of cancer and/or cancer metastasis and a diagnostic agent for cancer comprising the same as an active ingredient.

The present invention provides DNA aptamer specifically binding to periostin, an inhibitor of cancer or cancer metastasis or a composition for diagnosis of cancer or cancer metastasis comprising the same as an active ingredient, and a method for inhibiting (treating) cancer or cancer metastasis and a method for diagnosis of cancer using the same.

The periostin may be derived from mammals, preferably human, and for example, it may be Accession no. NP_Q15063-human, NP_056599-mouse, NP_001102020.1-rat, and the like, for example, NP_Q15063-human (human periostin).

The periostin aptamer may comprise modified bases, it may have a total base length of 25 to 100, preferably 30 to 80, more preferably 35 to 50 including modified bases, and it specifically binds to periostin. In the periostin aptamer of the present invention, bases other than the modified bases, unless otherwise described, are selected from the group consisting of A, G, C, T, and deoxy forms thereof (for example, 2'-deoxy form).

The modified base refers to a modified form that is substituted at 5-position of dU (deoxyuracil) with a hydrophobic functional group, and it may be used instead of base 'T'. The hydrophobic functional group may be at least one selected from the group consisting of a naphthyl group, a benzyl group, a pyrrole benzyl group, and tryptophan, and the like. As such, since the 5-position of dU base is substituted with a hydrophobic functional group and modified, affinity with periostin remarkably increases compared to non-modified case.

The number of modified bases in the periosin aptamer may be 5 to 20, preferably 10 to 17.

In a specific embodiment, the periostin aptamer may have a total base length of 25 to 80, preferably 30 to 65, more preferably 35 to 50, including at least one nucleotide sequence selected from the group consisting of SEQ ID NO: 5 to SEQ ID NO: 40 (in the nucleotide sequence 'n' is the modified base or 'T', specifically the modified base).

In a specific embodiment, the periostin aptamer may consist only of at least one nucleotide sequence selected from the group consisting of SEQ ID NO: 5 to SEQ ID NO: 40, or it may further comprise a nucleotide sequence consisting of 3 to 25, specifically 5 to 20 bases at the 5'terminal, 3'terminal or both terminals of the nucleotide sequence, thus having a total base length of 30 to 120, 35 to 100, or 45 to 90. The nucleotide sequence further included in the 5'terminal, 3'terminal or both terminals may be selected from the group consisting of SEQ ID NO: 1 to SEQ ID NO: 4. For example, the periostin aptamer may include ACGAG (SEQ ID NO: 1) at the 5'terminal of at least one nucleotide sequence selected from the group consisting of SEQ ID NO: 1 to SEQ ID NO: 40, and AACAA (SEQ ID NO: 2) at the 3'terminal, or it may include GATGTGAGTGTGTGACGAG (SEQ ID NO: 3) at the 5'terminal and AACAACAGAACAAGGAAAGG (SEQ ID NO: 4) at the 3'terminal, but is not limited thereto.

In a specific embodiment, the periostin aptamer of the invention may have a nucleotide sequence of the following SEQ ID NO: 45 or SEQ ID NO: 46:

(SEQ ID NO: 45)
5'-ACGAG-[N]-AACAA-3'

(N is a variable core sequence of the aptamer, and consists of 25 to 80, preferably 30 to 65, more preferably 35 to 50 bases, and each base is independently selected from the group consisting of A, C, G, deoxy forms thereof, and modified bases that are substituted at 5'-position of dU (deoxyuracil) with a hydrophobic functional group (for example, at least one selected from the group consisting of a naphthyl group, a benzyl group, a pyrrole benzyl group, and tryptophan)).

(SEQ ID NO: 46)
5'-GATGTGAGTGTGTGACGAG-[N]-AACAACAGAACAAGGAAAGG-3'

(N is a variable core sequence of the aptamer, and consists of 25 to 80, preferably 30 to 65, more preferably 35 to 50 bases, and each base is independently selected from the group consisting of A, C, G, deoxy forms thereof, and modified bases that are substituted at 5'-position of dU (deoxyuracil) with a hydrophobic functional group (for example, at least one selected from the group consisting of a naphthyl group, a benzyl group, a pyrrole benzyl group, and tryptophan)).

As explained above, the N may be selected from the group consisting of SEQ ID NO: 5 to SEQ ID NO: 40.

In the nucleotide sequence described herein and in the attached nucleotide sequence (SEQ ID NO: 5 to SEQ ID NO: 44), 'n', unless otherwise described, refers to 'T' or a modified form of dU (deoxyuracil) that is substituted at the 5'position with a hydrophobic functional group, preferably a modified form of dU (deoxyuracil) that is substituted at the 5-position with a hydrophobic functional group. The hydrophobic functional group is at least one selected from the group consisting of a benzyl group, a naphthyl group, a pyrrole benzyl group, tryptophan, and the like.

And, the periostin aptamer may be modified at the 5'terminal, 3'terminal or both terminals so as to improve serum stability (see Examples 2, 3 and 4). The periostin aptamer may be modified by binding of at least one selected from the group consisting of PEG (polyethylene glycol), idT (inverted deoxythymidine), LNA (Locked Nucleic Acid), 2'-methoxy nucleoside, 2'-amino nucleoside, 2'F-nucleoside, amine linker, thiol linker, and cholesterol and the like to 5'terminal, 3'terminal or both terminals. In a preferable embodiment, the periostin aptamer may include PEG (polyethylene glycol; for example, molecular weight 500-50,000 Da) attached to the 5'terminal, idT (inverted deoxythymidine) attached to the 3'terminal, or PEG (for example, molecular weight 500-50,000 Da) attached to the 5'terminal and idT (inverted deoxythymidine) attached to 3'terminal.

The 'idT (inverted deoxythymidine)' is one of the molecules used to prevent decomposition of aptamer with low nuclease resistance by nuclease. Although nucleic acid unit binds 3'-OH of the previous unit with 5'-OH of the next unit to form a chain, idT binds 3'-OH of the previous unit with 3'-OH of the next unit to cause artificial change so that 5'-OH is exposed instead of 3'-OH, thereby inhibiting decomposition by 3'exonuclease, which is a kind of nuclease.

It was confirmed that the periostin aptamer of the present invention exhibits remarkable effects for inhibiting adhesion, migration and invasion as well as growth of cancer cells (see Example 5 to 8).

Thus, another embodiment provides a pharmaceutical composition for treating cancer and/or inhibiting cancer metastasis, comprising the above explained periostin aptamer as an active ingredient. The pharmaceutical composition may further comprise a pharmaceutically acceptable carrier. Still another embodiment provides a method for treating cancer and/or inhibiting cancer metastasis, comprising the step of administering a pharmaceutically effective amount of the above explained periostin aptamer to a patient in need of treatment of cancer and/or inhibition of cancer metastasis. The method may further comprise a step of confirming a patient in need of treatment of cancer and/or inhibition of cancer metastasis, before the administration step. Still another embodiment provides use of the above explained periostin aptamer for treatment of cancer and/or inhibition of cancer metastasis.

The periostin aptamer or a pharmaceutical composition comprising the same may be formulated into various dosage forms for oral administration or parenteral administration.

For example, it may be formulated into any dosage form for oral administration such as a tablet, a pill, a hard/soft capsule, liquid, suspension, emulsion, syrup, granules, elixirs, and the like. The dosage form for oral administration may comprise a pharmaceutically acceptable carrier such as diluents such as lactose, dextrose, sucrose, mannitol, sorbitol, cellulose, and/or glycine, or slip modifiers such as silica, talc, stearic acid, and a magnesium salt or calcium salt thereof and/or polyethylene glycol and the like, in addition to the active ingredient, according to the common composition of each dosage form.

And, in case the dosage for oral administration is a tablet, it may comprise a binder such as magnesium aluminum silicate, starch paste, gelatin, tragacanth, methylcellulose, sodium carboxymethylcellulose and/or polyvinylpyrolidine and the like, and if necessary, may comprise a disintergrating agent such as starch, agar, alginic acid or a sodium salt thereof, or a boiling mixture and/or absorbent, a coloring agent, a flavoring agent, or a sweetener, and the like.

And, in case the periostin aptamer or a pharmaceutical composition comprising the same is formulated into a dosage form for parenteral administration, it may be administered by parenteral administration route such as subcutaneous injection, intravenous injection, intramuscular injection, intrathoracic injection, and the like. In order to formulate into the dosage form for parenteral administration, the pharmaceutical composition may be mixed with an active ingredient, namely periostin aptamer together with a stabilizer or buffer in water to prepare a solution or a suspension, and the solution or suspension may be prepared into a unit dosage form of an ampoule or a vial.

And, the pharmaceutical composition may be sterilized, or further comprise adjuvants such as an antiseptic, a stabilizer, water dispersible powder or an emulsifier, a salt for regulation of osmotic pressure, and/or buffer and the like, and may further comprise other therapeutically useful materials, and it may be formulated by a common method of mixing, granulation or coating.

And, the term "pharmaceutically effective amount" means the amount of an active ingredient that can exhibit desired effects, namely, effects for prevention and/or treatment of cancer, or inhibition of cancer metastasis. The active ingredient, namely periostin aptamer may be included in the pharmaceutical composition in an effective amount of 0.1 to 500 mg/kg (body weight), preferably 0.5 to 100 mg/kg (body weight) per day, and the pharmaceutical composition may be divided into two or more times per day and administered by oral or parenteral route.

The cancer that can be treated or of which metastasis can be inhibited by the periostin aptamer or pharmaceutical composition comprising the same of the present invention may include all kinds of cancers, and for example, it may be at least one selected from the group consisting of breast cancer, colorectal cancer, lung cancer, gallbladder cancer, pancreatic cancer, stomach cancer, uterine cancer, head and neck squamous cell carcinoma, prostate cancer, and glioblastoma.

The administration subject of the periostin aptamer or pharmaceutical composition comprising the same of the present invention may be mammals including human, and preferably, it may be rodents or human.

And, since the overexpression of periostin is observed in patients with various solid cancers including breast cancer and colorectal cancer and cancer metastasis, the periostin aptamer may be used as a composition for diagnosis of cancer and/or cancer metastasis.

According to another embodiment, provided are use of the periostin aptamer for diagnosis of cancer and/or cancer metastasis, and a method for providing information on the diagnosis of cancer and/or cancer metastasis using the periostin aptamer.

The method for providing information on the diagnosis of cancer comprises reacting a patient's biological sample with the periostin aptamer; and measuring the binding degree of periostin aptamer in the biological sample, wherein if the binding degree of periostin aptamer in the patient's biological sample is higher than a normal sample, the patient is judged as a cancer patient. Thus, the method may further comprise a step of measuring the binding degree of periostin aptamer in a normal sample.

The patient may be mammals including human, preferably rodents or human, and it means a subject in which cancer development or cancer metastasis is judged.

The cancer, on the diagnosis of which information can be provided by the method may include all kinds of cancer, and for example, it may be at least one selected from the group consisting of breast cancer, colorectal cancer, lung cancer, gallbladder cancer, pancreatic cancer, stomach cancer, uterine cancer, head and neck squamous cell carcinoma, prostate cancer, and glioblastoma.

The normal sample may be obtained from mammals including human, preferably from rodents or human, and it means a biological sample obtained from a subject without development of cancer, on the diagnosis of which information is provided, for example, cancer selected from the group consisting of breast cancer, colorectal cancer, lung cancer, gallbladder cancer, pancreatic cancer, stomach cancer, uterine cancer, head and neck squamous cell carcinoma, prostate cancer, and glioblastoma, or metastasis thereof.

The biological sample may be a mammal body except human, cells, tissues, blood, saliva and the like separated from mammals including human.

The step of measuring the binding degree of periostin aptamer in the biological sample may be conducted by measuring technology of DNA aptamer binding commonly used in related technological field, and for example, the end of the periostin aptamer may be labeled with fluorescent or radioactive material or bound with biotin to measure the intensity of fluorescence or radioactivity, or it may be imaged and observed, but is not limited thereto.

According to one specific embodiment, among the periostin aptamers, one pair of aptamers that have different binding regions with periostin and do not hinder binding each other are selected, one is fixed on a substrate (capture aptamer), and the other (detection aptamer) is labeled with fluorescent or radioactive material (or bound with material capable of reacting fluorescent or radioactive material) at the end, and the intensity is measured, thereby measuring whether or not periostin exists in the sample or whether or not periostin is overexpressed.

As such, when the existence of periostin in the sample or overexpression of periostin is confirmed using aptamer, remarkably excellent sensitivity is shown compared to detection using the existing antibodies.

The novel DNA aptamer of the present invention that binds to periostin and inhibits the activity also binds to purified protein as well as periostin expressed on the surface of cancer cells (Kd≈4 nM). The aptamer of the present invention may also bind to mouse periostin and other proteins having structural similarity with periostin such as βIG-H3. The aptamer of the present invention may specifically bind to all kinds of cells expressing periostin on the cell surface, and it inhibits periostin-mediated signal pathways. And, it was confirmed that the aptamer of the present invention effectively inhibits adhesion, migration and invasion of solid cancer such as breast cancer. The data strongly shows various biomedical applicabilities of the aptamer of the present invention in periostin targeted therapy and diagnosis.

Breast cancer is most common cancer and the second cause of cancer death. Cancer metastasis is the main cause of cancer related death. Particularly, most breast cancer patients are often diagnosed after metastasis is progressed, and show about 80% recurrence rate despite of surgery and chemotherapy. Thus, treatment of cancer metastasis is the major target of cancer treatment. Cancer cells should overcome various kinds of stresses and rate-limiting steps so that metastasis grows in the microenvironment of new organ. Molecules overexpressed in cancer cells such as periostin are known to promote the progression to metastasis and malignant tumor. Periostin is considered as a strong target for treatment of solid cancer such as breast cancer because it performs an important function in angiogenesis and metastasis and has good accessibility as extracellular matrix protein. Some antibodies to periostin have been suggested as an anticancer agent- or radioisotope-carrier as well as treatment strategy of human cancer including metastasis. Particularly, antibodies targeting periostin in vitro influence on the proliferation, migration, invasion and adhesion of cancer cells, and in vivo have antiproliferation and antimetastasis effect. However, since these antibodies have low affinity (uM range Kd) and undesirable pharmacokinetical properties (for example, have low tumor invasion capacity and are rapidly removed), they have a limitation in the application for target delivery, and thus, development of high affinity molecules with improved pharmacokinetic properties and serum stability is becoming important.

Meanwhile, DNA aptamer can be chemically synthesized and be easily modified for in vivo application, and has excellent tumor tissue penetration. Thus, DNA aptamer has various advantages as an anticancer molecule. Since natural oligonucleotide is sensitive to hydrolysis by nuclease, stabilization of phosphate backbone is the main point for biomedical application of DNA aptamer. Although DNA aptamer is modified with a neutral group such as methyl phosphonate and phosphoramidate to increase the nuclease resistance, the modified DNA aptamer shows lower binding affinity than non-modified DNA Aptamer. In order to increase binding affinity and offset slow off-rate, SELEX was conducted with modified nucleotides using various functional groups. The obtained data shows that DNA aptamer modified with a benzyl group shows high affinity with periostin (1 nM) and that cross-reactivity is minimized. Due to the potential morphological difference between purified protein and endogenous protein, selected aptamers cannot always bind to the target protein when in vivo applied. Thus, in order to identify aptamer showing in vivo activity, it is necessary to integrate in vivo related conditions into a screening process. The novel periostin DNA aptamer (PNDA-3) of the present invention specifically binds to periostin expressed on the surface of breast cancer cells, while it does not bind to periostin-negative cell line. The major riskiness of cell-based approach is that the species of originating organisms of the cells for screening and the species of test animal models for confirmation of in vivo binding are different each other. Although use of human cells or human cell line for ligand screening accords with ultimate biomedical application, ligand binding specificity and affinity to a target molecule cannot be sufficiently proved in a test animal model, and preclinical studies cannot be conducted. Thus, in the present invention, aptamer binding to various proteins having structural homogeneity was tested. Despite the difference between species of human and mouse, aptamer binds to the two kinds of proteins, which is thought to be due to high sequence and structural homogeneity (92%) between human periostin and mouse periostin. As such, since aptamer binds to periostin non-dependently upon the species, the properties of the ligand can be confirmed in various mouse disease models and provided for biomedical use. In human, four proteins including fas-1 domain are known. βIG-3H and periostin are secretory proteins having 4 fas-1 domains, and stabilin-1 and stabilin-2 are membrane proteins having 7 fas-1 domains. Although the biological functions of these proteins have not been completely found, since all fas-1 domains include integrin-interactive tyrosine-hystidine (YH) motif, a possibility of functioning for regulating cell-matrix interaction is suggested. The aptamer of the present invention blocks interaction between periostin and integrin. By completely inhibiting binding of periostin to integrin on the surface of cell line and inhibiting the interaction, the aptamer of the present invention functionally blocks the action of periostin.

And, the separated aptamer of the present invention may be useful for diagnosis of periostin-mediated metastasis or molecular level imaging. The aptamer specifically binds to mouse periostin as well as human periostin. The expression of periostin is not detected in immortalized cell line derived from normal breast tissue or normal breast epithelial cell. However, according to gene array data and proteomic analysis data, in the majority of breast cancer samples, the expression of periostin is increased 20 times or more, compared to normal breast tissue. And, in the case of breast cancer patient with bone metastasis, serum concentration of periostin is significantly increased. Thus, the aptamer can be usefully used for in vitro measurement of the possibility of metastasis and cancer prognosis in cancer patients. In the present invention, biotin-labeled aptamer may be used to specifically detect periostin from various protein mixtures. And, fluorescent substance (Cy3-)-bound aptamer can specifically detect periostin in tissues separated from a breast cancer metastasis mouse model and a practical breast cancer patient. Compared to antibody, the DNA aptamer of the present invention shows rapid uptake by tumor (=>tumor cells), more rapid blood removal and more continuous tumor retention, thus enabling remarkable imaging with higher ratio of tumor to blood. Thus, the aptamer of the present invention can be usefully used for in vivo imaging of periostin secreting cells in tumor metastasized body microenvironment.

Secreted periostin acts as cytokine for signal transduction through cell adhesion proteins and cell adhesion molecules ($\alpha_v\beta_3$ and $\alpha_v\beta_5$ integrins). Periostin promotes recruitment of EGFR (epidermal growth factor receptor) and activation of Akt/PKB and FAK-mediated signaling pathways. The aptamer of the present invention inhibits activation of intracellular signal by inhibiting binding of periostin to integrin.

In the present invention, it was confirmed by TIR fluorescent microscope that the aptamer binds to periostin expressed on the surface of cell and inhibits interaction with integrin. And, as the result of confirming binding capacity using domain deleted mutant proteins, it could be seen that the aptamer binds to fas-1 domain, which is important for binding with intergin.

Stimulation of integrins $\alpha_v\beta_3$ and $\alpha_v\beta_5$ activates PI-3 kinase and FAK-mediated signaling pathways. Consistently, in breast cancer cell lines 4T1, MDA-MB-231, the aptamer strongly decrease FAK and Src phosphorylations induced by periostin. Periostin has been reported to activate Akt/PKB signaling pathway through integrin $\alpha_v\beta_3$ to improve cancer cell survival in colon cancer. However, the treatment of the aptamer of the present invention does not influence on the Akt phosphorylation and cell survival. Thus, it can be explained that the FAK and Src phosphorylation inhibiting capacity of the aptamer is due to the inhibition of the formation of periostin-integrin complex.

Various results have been reported with regard to the role of periostin in cancer cell proliferation. Proliferations of colorectal cancer cells and cholangiocanrcinoma cells are induced by the addition of recombinant periostin. To the contrary, the aberrant expression of periostin in ovarian cancer cell line and breast cancer cell line does not influence on cell proliferation or rather inhibits cell proliferation. Recent study results using pancreatic cancer cells suggest that periostin can exert biphasic effects in tumorigenesis. The in vitro cell proliferation data presented in the present invention shows that the aptamer of the present invention does not influence on cell proliferation, which means that periostin is not a pro-proliferation factor in breast cancer.

The overexpression of periostin influences on metastasis-related functions as well as cancer growth. Clinical data shows that the overexpression of periostin is found a lot in end-stage cancer patients, and that it is also related to a bad prognosis of patients. And, in case periostin-overexpressing cancer cell line is injected into a mouse model, promotion of cancer metastasis is observed. Recently, it is being reported that an EMT (epithelial-mesenchymal transition) process corresponding to the beginning of metastasis is regulated by periostin. Periostin promotes cancer cell adhesion, migration and invasion, which are the main functions of cancer metastasis. In the present invention, it was confirmed that periostin-induced cancer cell adhesion, migration and invasion are inhibited by periostin aptamer treatment. Namely, the aptamer has a function for inhibiting cancer metastasis.

In conclusion, the aptamer is useful as the leading compound for designing a novel kind of anticancer agent, and it can be added to repertory of inhibitors targeting periostin-overexpressing cancer. The present invention suggests that aptamer inhibiting the function of periostin has remarkable inhibition effect in breast cancer metastasis, for the first time.

Advantageous Effect of the Invention

The periostin aptamer provided in the present invention inhibits interaction of periostin and integrin to block signaling pathway, and inhibits cancer cell adhesion, proliferation, migration and invasion, and thus, it can be usefully used as an anticancer agent and/or for diagnosis of cancer.

MODE FOR INVENTION

Figure 1:
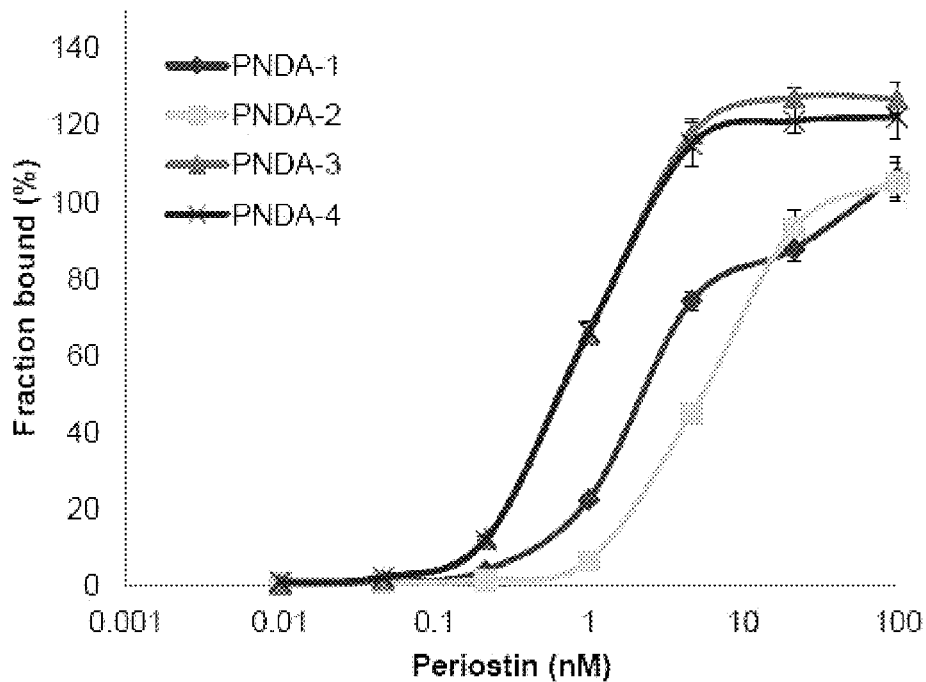
FIG. 1 shows binding capacity of the periostin DNA aptamer (PDNA) according to one example with periostin protein, and shows the results of binding affinity measured using $^{32}$P-labeled PNDA and various concentrations of human recombinant periostin (up to 100 nM).

Hereinafter, the present invention will be explained in detail with reference to Examples, Comparative Examples and Experimental Examples. However, these Examples, Comparative Examples and Experimental Examples are provided only to aid in understanding of the invention, and the category and scope of the invention is not limited thereto.

REFERENCE EXAMPLE

Preparation of Antibody and Reagent

Human periostin protein and mouse periostin protein were purchased from R&D system (Minneapolis, Minn.). Integrin α$_v$β$_3$ and α$_v$β$_5$ antibodies were purchased from Millipore (Temecula, Calif., USA). Antibodies used for Western blot are as follows: Anti-ERK, phosphor-ERK, AKT, phosphor-AKT, FAK, phosphor-FAK, SRC, phosphor-SRC Ab (cell signaling, Beverly, Mass.), beta-actin Ab (Santa Cruz Biotechnology, Santa Cruz, Calif.).

Cell Culture

MCF7, MDA-MB-231 human breast cancer cell line, 4T1 mouse breast cancer cell line and human embryonic kidney cells 293T were obtained from American Type Culture Collection (Manassas, Va., USA). MCF7 cells were cultured in a RPMI-1640 (Lonza) medium supplemented with 10% fetal bovine serum (Gibco), penicillin (100 units/ml, Gibco), and streptomycin (100 units/ml, Gibco) at 37° C. and 5% $CO_2$ conditions. MDA-MB-231, HEK 293T, 4T1 cells were cultured in Dulbecco's modified Eagle's medium (Lonza) supplemented with 10% fetal bovine serum (Gibco), penicillin (100 units/ml), and streptomycin (100 units/ml) at 37° C. and 5% $CO_2$ conditions. To deprive serum, MCF7, MDA-MB 231, and 4T1 cells were washed with 1×PBS three times and incubated in a serum-free medium (DMEM or RPMI-Lonza) at 37° C. for 20 hours, and the above prepared periostin, integrin antibodies and the following aptamer were treated by the method described in each example below.

Example 1

In Vitro Selection of Anti Periostin DNA Aptamer

To prepare single strand modified DNA library required for SELEX, antisense library with biotin at 5'[5'-biotin-d (CCTTTCCTTGTTCTGTTGTT-N40-CTCGTCACA-CACTCACATC)-3' (SEQ ID NO: 47)] was synthesized. The antisense library was reacted with 50 uM 5' primer (GATGTGAGTGTGTGACGAG; SEQ ID NO: 48), 0.5 mM dNTP (ATP, GTP, CTP, Bz-dU), 0.25 U/ul KOD XL (Invitrogen), 10× extension buffer (1.2M Tris-HCl pH7.8, 100 mM KCl, 60 mM $(NH_4)_2SO_4$, 70 mM $MgSO_4$, 1% Triton X-100, 1 mg/ml BSA) at 70° C. for 1 hr to prepare double strand DNA. Single strand modified DNA library was eluted using 20 mM NaOH, and then, neutralized with a HCl solution. 1 nmole of the synthesized library was put in selection buffer (200 mM HEPES, 510 mM NaCl, 25 mM KCl, 25 mM $MgCl_2$), reacted at 95° C., 70° C., 48° C., 37° C. respectively for 5 minutes, and then, for negative selection, mixed with 10 μL of 10× protein competition buffer (10 μM prothrombin, 10 μM casein, 0.1% (w/v) HSA (human serum albumin, SIGMA), and then, added to Talon bead (50% (w/v) slurry to which supernatant-removed Hexa-His is bound and reacted at 37° C. for 10 minutes.

After negative selection reaction, only supernatant was taken and transferred to a new tube, and then, reacted in periostin-bound Talon bead at 37° C. for 1 hour. Talon bead bound with DNA-periostin complex was washed with 100 μL of selection buffer (200 mM HEPES, 510 mM NaCl, 25 mM KCl, 25 mM $MgCl_2$) 5 times. At $5^{th}$ washing, it was transferred to a new plate and washed. 85 μL of a 2 mM NaOH solution was added to elute target-binding library, and then, neutralized with 20 μL of a 8 mM HCl solution.

The target-binding library DNA was amplified using QPCR (quantitative PCR, IQ5 multicolor real time PCR detection system, Bio-rad). Each 5 uM of 5' primer (GATGTGAGTGTGTGACGAG (SEQ ID NO: 48) and 3' primer (Biotin-CCTTTCCTTGTTCTGTTGTT, Biotin-SEQ ID NO: 49) (5×QPCR master Mix, Novagen), 0.075 U/ul KOD (Novagen), 1 mM dNTP (Roche Applied science), 25 mM $MgCl_2$, 5×SYBR green I (Invitrogen) were mixed so that total volume became 125 μL, and 1 cycle of 96° C. 15 seconds, 55° C. 10 seconds and 68° C. 30 minutes, and 30 cycles of 96° C. 15 seconds and 72° C. 1 minutes were repeated to prepare double strand library.

The DNA library prepared by QPCR was mixed with 25 μL Myone SA bead (Invitrogen) at room temperature for 10 minutes to fix. The amount of mixed DNA was 60 ul QPCR product. A 20 mM NaOH solution was added to prepare single strand DNA. And, DNA comprising modified nucleic acid was synthesized by the same method as preparation of the library and used in the next round. Total 8 SELEX rounds were conducted, and for more selective binding, from $4^{th}$ to $6^{th}$ and $7^{th}$ to $8^{th}$ rounds, DNA-protein (periostin) complex was diluted in a 10 mM $DxSO_4$ (sigma) solution to 1/200, 1/400 and DNA aptamer was selected.

Example 2

Selection of DNA Aptamer Interacting with Periostin and Interaction Test

After successfully conducting SELEX rounds, the finally obtained DNA pool was cloned using TA cloning kit (SolGent). And, it was sequenced with M13 primer (CAGGAAACAGCTATGAC; SEQ ID NO: 50) existing on a vector to obtain the following sequence. DNA aptamer that highly specifically binds to the obtained periostin has a nucleotide sequence of 5'-GATGTGAGTGTGTGACGAG-[Core sequence]-AACAACAGAACAAGGAAAGG-3' (SEQ ID NO: 46), wherein the core sequence is as shown in the following Table 1, and n represents Benzyl-dU.

TABLE 1

| No of clone | SEQ ID NOs. | Core Sequence |
|---|---|---|
| 1 | SEQ ID NO: 5 | nCnGGnCCnnCCnGnAnnAGAnCAnAnC CnnAGGnAnCGnC |
| 2 | SEQ ID NO: 5 | nCnGGnCCnnCCnGnAnnAGAnCAnAnC CnnAGGnAnCGnC |
| 3 | SEQ ID NO: 6 | nCACACGnnGAnGACnGGAnGGnAGnnA AAGAGGGnGGGGC |
| 4 | SEQ ID NO: 7 | nCnGAnCCnnCCnGnAnnAGAnCAnAnC nnCAGGnAnCGnC |
| 5 | SEQ ID NO: 8 | nCnGGnCCnnCCnnnGACGACnAnnGnn nGGnAnCGGACAAC |
| 6 | SEQ ID NO: 9 | nCnGGnCCnnCCnnnGACGACnAnnGnn nGGnAnCGGnCAAC |
| 7 | SEQ ID NO: 6 | nCACACGnnGAnGACnGGAnGGnAGnnA AAGAGGGnGGGGC |
| 8 | SEQ ID NO: 10 | nnGnCGCAnGnGCGGnnCAGnCnGGnCC nnCAGCACCGnAC |
| 9 | SEQ ID NO: 11 | nCnGGnCCnnCCCAnAnnAGAnCAnAnC CnCGGGnAnCGnC |
| 10 | SEQ ID NO: 12 | CCnGCGCGnnnCAAnnnAnnCCCACAnA CCCnCAnAAGCC |
| 11 | SEQ ID NO: 13 | nnGnCGCAnGnGCGGnnCAGnCnGGnCC nnCAGCACCGnGC |
| 12 | SEQ ID NO: 9 | nCnGGnCCnnCCnnnGACGACnAnnGnn nGGnAnCGGnCAAC |

TABLE 1-continued

| No of clone | SEQ ID NOs. | Core Sequence |
|---|---|---|
| 13 | SEQ ID NO: 14 | nnGnCGAAAnnnGGnAnGAGnAGGnnGnAGGnAGAGCCCGC |
| 14 | SEQ ID NO: 15 | nCnGGnCCnnCCnGnAnnAGAnCAnAnCCnCAGGnAnCGnC |
| 15 | SEQ ID NO: 9 | nCnGGnCCnnCCnnnGACGACnAnnGnnnGGnAnCGGnCAAC |
| 16 | SEQ ID NO: 16 | nCnGGnCCnnCCnnnGACnACnAnnGnnnGGnAnCGGnCAAC |
| 17 | SEQ ID NO: 17 | nCnGGnCCnnCCnCCCnAAnnGCnGnnGAGGnAnCGGnAC |
| 18 | SEQ ID NO: 18 | nCCGGnCnGAnnnCCAACAnnnGnCCnAnCCCnGAnCGnCC |
| 19 | SEQ ID NO: 19 | nCnGAnCCnnCCnCCCnAAnnGCnGnnGAGGnAnCGGnCAC |
| 20 | SEQ ID NO: 20 | nCnGGnCCnnCCnCnnnGnCCCCGAnAGGGnAnGGnAnCGC |
| 21 | SEQ ID NO: 21 | nCACACGnnGAnGACnGGAnGGnAGnnAAAGAGGGnGGGGC |
| 22 | SEQ ID NO: 15 | nCnGGnCCnnCCnGnAnnAGAnCAnAnCCnCAGGnAnCGnC |
| 23 | SEQ ID NO: 22 | GGnCnGGnCCnnAAGAnGnnCGnAnCGnACGAGCnCCCnAC |
| 24 | SEQ ID NO: 15 | nCnGGnCCnnCCnGnAnnAGAnCAnAnCCnCAGGnAnCGnC |
| 25 | SEQ ID NO: 23 | nCnGGnCCnnCCnnnGACGACnAnnGnnnGGnAnCGGnC |
| 26 | SEQ ID NO: 6 | nCACACGnnGAnGACnGGAnGGnAGnnAAAGAGGGnGGGGC |
| 27 | SEQ ID NO: 24 | GCGACnGGGCGAGGCnnGGGAnGGGnnACGCCGnGCAGC |
| 28 | SEQ ID NO: 25 | AAGCnnCGGnCnGGnCCnnCCCCCCnGGCnnnGGCnCnAAGGGGCCGCC |
| 29 | SEQ ID NO: 26 | AAGGCACACCnCGCACAnGnnAACnACnACnGACACnCC |
| 30 | SEQ ID NO: 27 | nnGnCACAnGnGCGGnnCAGnCnGGnCCnnCCGCACCGnAC |
| 31 | SEQ ID NO: 28 | nnAnCACAnGnGCGGnnCAGnCnGGnCCnnCAGCACCGnGC |
| 32 | SEQ ID NO: 29 | CnAnAAACnCGnnGCCCCCnCACAGCnGCAAnACAnCnCGGC |
| 33 | SEQ ID NO: 12 | CCnGCGCGnnnCAAnnnAnnCCCACAnACCCnCAnAAGCCC |
| 34 | SEQ ID NO: 15 | nCnGGnCCnnCCnGnAnnAGAnCAnAnCCnCAGGnAnCGnC |
| 35 | SEQ ID NO: 30 | AAGCnnCGGnCnGGnCCnnCCCCCCnGCnnnGGCnCnAAGGGGGCCGCn |
| 36 | SEQ ID NO: 31 | nGnAAGnGnnnnCnAnCAnnnAAnGnnnGCAGACCGnnGAC |
| 37 | SEQ ID NO: 32 | nGnGnGnGnnnnnnGnGGnCnnAAnCAnGCAGCnGnGnnGC |
| 38 | SEQ ID NO: 33 | nCnGGnCCnnCCnnnGACGACnAnnGnnnGGnAnCGAnCAAC |
| 39 | SEQ ID NO: 14 | nnGnCGAAAnnnGGnAnGAGnAGGnnGnAGGnAGAGCCCGC |
| 40 | SEQ ID NO: 15 | nCnGGnCCnnCCnGnAnnAGAnCAnAnCCnCAGGnAnCGnC |
| 41 | SEQ ID NO: 34 | nCAAnnnnGGnGCCnGGnGGCnnnACCGAnnGCGCACGC |
| 42 | SEQ ID NO: 17 | nCnGGnCCnnCCnCCCnAAnnGCnGnnGAGGnAnCGGnAC |
| 43 | SEQ ID NO: 6 | nCACACGnnGAnGACnGGAnGGnAGnnAAAGAGGGnGGGGC |
| 44 | SEQ ID NO: 35 | nCAAnnnnGGnGCnnGGnGGCCnnnACCGAnnGCGCACGC |
| 45 | SEQ ID NO: 36 | nCGACnAnCGAGnnnCAAnnnAnnCCCCCACnCACAAnCnC |
| 46 | SEQ ID NO: 5 | nCnGGnCCnnCCnGnAnnAGAnCAnAnCCnnAGGnAnCGnC |
| 47 | SEQ ID NO: 9 | nCnGGnCCnnCCnnnGACGACnAnnGnnnGGnAnCGGnCAAC |
| 48 | SEQ ID NO: 14 | nnGnCGAAAnnnGGnAnGAGnAGGnnGnAGGnAGAGCCCGC |
| 49 | SEQ ID NO: 37 | AAGCnnCGGnCnGGnCCnnCCCCCCnGGCnnnGGCnCnAAGGGGGCCGCC |
| 50 | SEQ ID NO: 38 | ACAACCCCnCAACnGCnAnCACnCnnGGCnCAACnAAnnAC |
| 51 | SEQ ID NO: 39 | nCnGGnCCnnCCnCnCnAAnnGCnGnnGAGGnAnCGGnAC |
| 52 | SEQ ID NO: 40 | nnGnCGCAnGnGCGGnnCAGnCnGGnCCnnCAGnACCGnAC |
| 53 | SEQ ID NO: 6 | nCACACGnnGAnGACnGGAnGGnAGnnAAAGAGGGnGGGGC |

In the example, n=Benzyl-dU [5-(N-Benzylcarboxyamide)-2'-deoxyuridine]

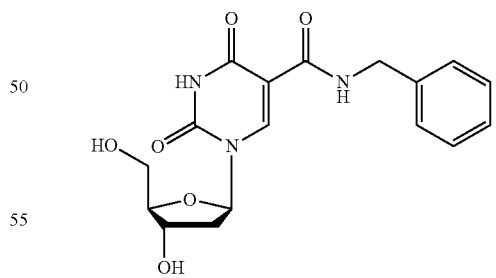

A=2'-deoxyAdenosine
G=2'-deoxyGuanosine
C=2'-deoxyCytidine
T=2'-deoxyThymidine (Thymidine)

The above discovered periostin aptamers were classified as a similar family as follows (Sequence homogeneity is based on 85% homogeneity of the nucleotide sequence):

TABLE 2

| number | Nucleotide Sequence | Clones |
|---|---|---|
| 10 | nCnGGnCCnnCCnGnAnnAGAnCAnAnC CnCAGGnAnCGnC (SEQ ID NO: 15) | 1, 2, 4, 9, 14, 22, 24, 34, 41, 46 |
| 2 | CCnGCGCGnnnCAAnnnAnnCCCACAnA CCCnCAnAAGCC (SEQ ID NO: 12) | 10, 33 |
| 5 | nnGnCGCAnGnGCGGnnCAGnCnGGnC CnnCAGCACCGnGC (SEQ ID NO: 13) | 8, 11, 30, 31, 52 |

TABLE 2-continued

| number | Nucleotide Sequence | Clones |
|---|---|---|
| 8 | nCnGGnCCnnCCnnnGACGACnAnnGnn nGGnAnCGGnCAAC (SEQ ID NO: 9) | 5, 6, 12, 15, 16, 25, 38, 47 |
| 3 | nnGnCGAAAnnnGGnAnGAGnAGGnnGn AGGnAGAGCCCGC (SEQ ID NO: 14) | 13, 39, 48 |
| 4 | nCnGGnCCnnCCnCCCnAAnnGCnGnnG AGGnAnCGGCnAC (SEQ ID NO: 17) | 17, 19, 42, 51 |
| 6 | nCACACGnnGAnGACnGGAnGGnAGnn AAAGAGGGnGGGGGC (SEQ ID NO: 21) | 3, 7, 21, 28, 43, 53 |
| 3 | AAGCnnCGGnCnGGnCCnnCCCCCCnG GCnnnGGCnCAAGGGGCCGCC (SEQ ID NO: 25) | 28, 35, 49 |
| 2 | nCAACnnnnGGnGCCnGGnGGCnnnnAC CGAnnGCGCACGC (SEQ ID NO: 34) | 41, 44 |

Several random sequences strongly binding to periostin were separated. After 8$^{th}$ SELEX round, 53 clones were sequenced. 5 distinct DNA sequences (DNA aptamers) to periostin were selected and filter binding assay was conducted. For this, DNA 1 µM, 0.25 µM, α-P$^{32}$ATP (5 pM, perkinelmer), 0.25 µL TdT, and 10×NEB buffer4(NEB) 10 µL were reacted at 37° C. for 30 minutes, and incubated at 70° C. for 10 minutes to inactivate TdT. DNA was purified using Micro spin G-50 column (GE healthcare). The labeled DNA 20,000 cpm was put in 100 µL of 1×SB buffer (200 mM HEPES, 510 mM NaCl, 25 mM KCl, 25 mM MgCl$_2$) and slowly cooled from 95° C. to 37° C. at 0.1° C./1 second. And, periostin was serially diluted at 100 nM to 12 points using buffer (200 mM HEPES, 510 mM NaCl, 25 mM KCl, 25 mM MgCl$_2$), and then, 30 µL of the heated and cooled DNA pool was respectively added and reacted at 37° C. for 30 minutes. Each 2 µL of the mixture of DNA and periostin was spotted to Nylon membrane (GE healthcare), and then, 5.5 µL of zorbax resin(Agilent) was added. And, it was put in a Durapore filter (Millipore) wetted with 50 µL of 1×SB buffer (200 mM HEPES, 510 mM NaCl, 25 mM KCl, 25 mM MgCl$_2$) beforehand, and vacuum was applied. And, the membrane filter was washed with 100 µL of 1× selection buffer (200 mM HEPES, 510 mM NaCl, 25 mM KCl, 25 mM MgCl$_2$). The filter plate was exposed to an image plate overnight, and then, the image was quantified with FLA-5100 (Fuji). The binding affinity was calculated from the value obtained through the filter binding assay using SigmaPlot 11 (Systat Software Inc.), and the results are shown in the following Table 3.

TABLE 3

| | clone # (SEQ ID NO) | | | | |
|---|---|---|---|---|---|
| | 17 (SEQ ID NO: 17) | 8 (SEQ ID NO: 10) | 3 (SEQ ID NO: 6) | 5 (SEQ ID NO: 8) | 1 (SEQ ID NO: 5) |
| Bmax (%) | 78 ± 1 | 81 ± 2 | 72 ± 2 | 80 ± 3 | 80 ± 3 |
| Kd(nM) | 0.63 ± 0.04 | 1.14 ± 0.19 | 0.54 ± 0.08 | 1.41 ± 0.25 | 0.60 ± 0.12 |

Bmax means the maximum extrapolated amount of DNA:protein complex, and as it is closer to 1, good performance is meant, and Kd (dissociation constant) is a value representing affinity, and the lower value means higher binding capacity.

Among the total clones, 4 aptamers were selected, and to increase binding affinity and specificity, the lengths were reduced from 80 nucleotides to 50 nucleotides, and they were named as 'PNDAs'. For this, synthesis was conducted while leaving each 5mer at the primer position, and binding capacity to periostin was measured. (see Table 4).

TABLE 4

| Clone# | Nucleotide Sequence (5' to 3') | B Max (%) | Kd (nM) |
|---|---|---|---|
| PNDA-1 | ACGAGnCnGGnCCnnCCnnnGACGACnAnn GnnnGGnAnCGAnCAACAACAA (SEQ ID NO: 41; Core seq-SEQ ID NO: 33) | 92 | 2.85 |
| PNDA-2 | ACGAGnCACACGnnGAnGACnGGAnGGnAG nnAAAGAGGGnGGGGCAACAA (SEQ ID NO: 42; Core seq-SEQ ID NO: 6) | 78 | 7.41 |
| PNDA-3 | ACGAGnnGnCGCAnGnGCGGnnCAGnCnGG nCCnnCAGCACCGnACAACAA (SEQ ID NO: 43; Core seq-SEQ ID NO: 10) | 95 | 1.07 |
| PNDA-4 | ACGAGnCnGGnCCnnCCnCCCnAAnnGCnG nnGAGGnAnCGGCnACAACAA (SEQ ID NO: 44; Core seq-SEQ ID NO: 17) | 90 | 1 |

In the Example, 'n' in the sequence represents Benzly-dU. The random sequence part of the aptamer (variable sequence, core sequence) is indicated by bold letters.

The Table 4 shows the PNDA sequences used in this experiment, and the experimental results in each sequence. Dissociation constants (Kd) and Bmax were calculated using SigmaPlot 11 (Systat Software Inc.). Among the selected aptamers, based on the $K_d$ value and B max value of PNDA-3, it can be considered as an appropriate candidate with the highest binding capacity.

FIG. 1 shows the results of binding affinity measured by the above method using $^{32}$P-labeled PNDA and various concentrations of human recombinant periostin (up to 100 nM), wherein binding assay was repeatedly conducted three times, and the mean value and the standard deviation were calculated according to the concentration of periostin and shown. The fraction bound of Y axis represents the binding degree of aptamer with protein as percentage, when the signal of p$^{32}$ labeled aptamer without protein is set as 0.

Figure 2A:
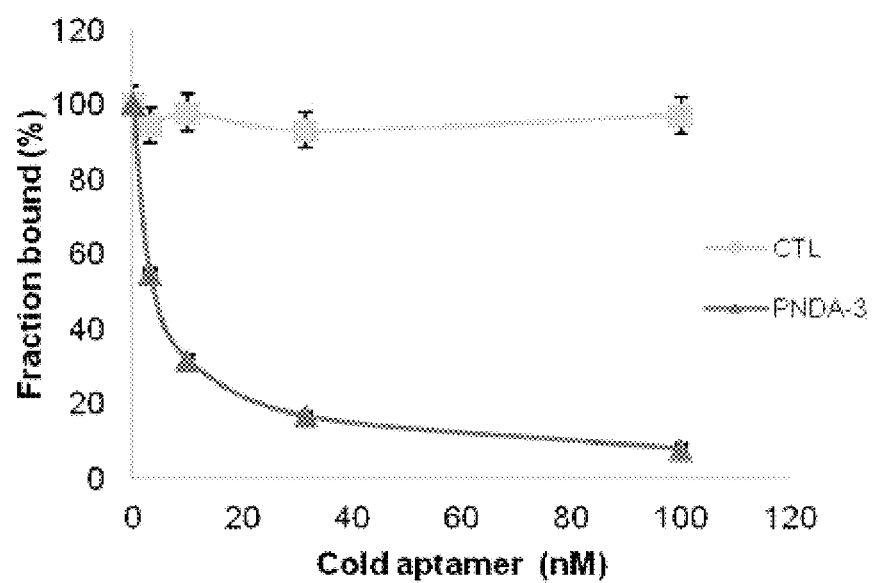
FIG. 2 shows specific interaction of the PNDA according to one example with periostin, wherein 2A is a graph showing competitive binding of PNDA to recombinant human periostin (rhPN), 2B is the result showing aptamer binding specificity with structurally similar proteins, and 2C and 2D are results showing that only periostin can be specifically detected in various pools of protein complexes using biotin-bound PDNA, and that such reaction is concentration-dependent.
Figure 2B:
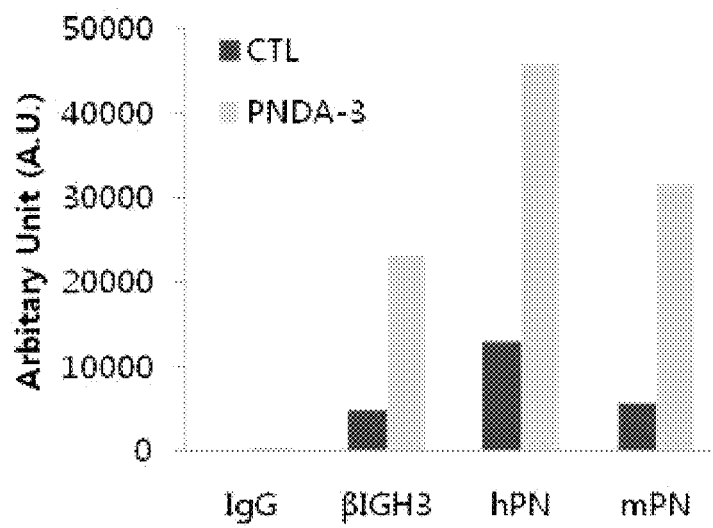

Meanwhile, specific interaction between PNDAs and periostin was additionally analyzed through competition assay. About 10 nM of [α-$^{32}$ P]-ATP-labeled PNDA-3 was reacted with periostin protein together with a specific competitor of non-radioisotope-labeled PNDA-3 or non-specific competitor (control aptamer), and the binding degree of DNA-protein complex was measured by the above described method. As the control (CTL) aptamer, ACGAGGnACG-GnGCnGAAGGACCAGACnGAACCGCACAnGCGA-CAAAACA A (SEQ ID NO: 51) was used (the same in the following examples). As the results, although the control aptamer does not influence on the binding of PNDA-3 with periostin, non-labeled PNDA-3 effectively decreases binding between the labeled PNDA-3 and periostin. Namely, specific binding of PNDA-3 to periostin was shown in FIG. 2A. In FIG. 2B, binding degrees of the aptamer to proteins having similar structures with human periostin (mouse periostin, human βIG-3H(R&D system), human IgG (Sigma)) were confirmed and compared. Although, PNDA-3 does not bind to human IgG protein, it binds to both human and mouse periostins. In addition, it was confirmed that human βIG-3H, though a little ratio, also binds to PNDA-3.

Since human periostin and mouse periostin show 90% or more amino acid sequence homogeneity, the cross linking therebetween is not unexpected.

Figure 2C:
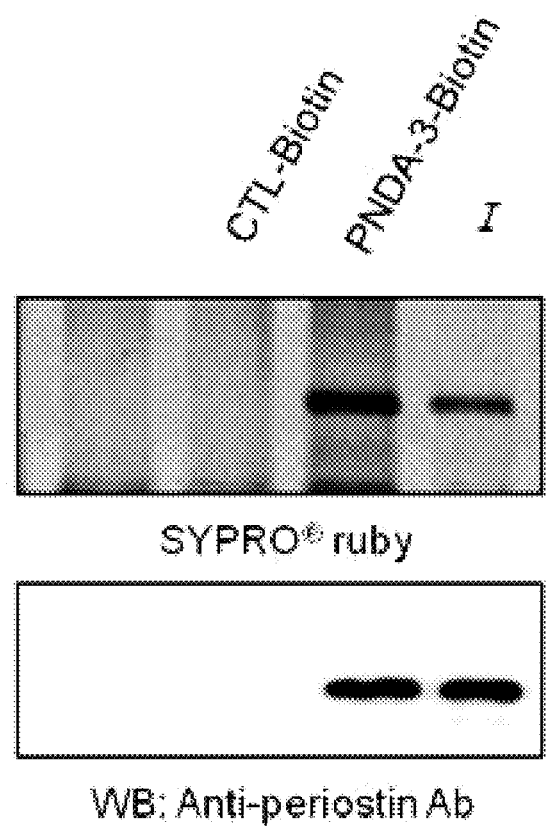
Figure 2D:
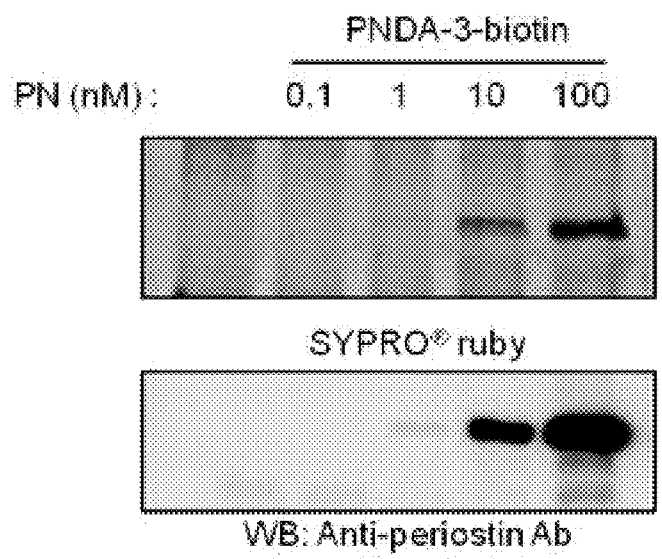

In order to confirm interaction between DNA aptamer and periostin under in vivo conditions, affinity purification was progressed. After adding 10 nM periostin to 10% (w/v) serum buffer (FBS solution, FBS-Gibco), it was reacted with the biotinylated aptamer for 1 hours, and then, the periostin-PNDA-3 complex was separated with steptavidin bead, and the existence of periostin was confirmed by SYPRO ruby staining and immunoblotting an shown in FIGS. 2C and 2D. As shown in FIGS. 2C and 2D, although control aptamer does not detect periostin existing in serum, PNDA-3 can specifically detect periostin. In FIG. 2C, I shows the result of loading ⅒ of the amount of periostin used in the experiment as control. It was also confirmed that the specific interaction between periostin and PNDA-3 increased in a dose-dependent manner.

These results show that the aptamer of the present invention specifically recognize periostin and has high affinity to periostin.

Example 3

Binding Inhibition Test of Aptamer to Cell Surface of Periostin

Due to the morphological difference between purified protein and protein expressed in cells, separated aptamers to purified protein does not always bind to the cells. Thus, binding capacity of aptamer to 4T1 breast cancer cells (periostin expressing cells) and MCF7 cells (periostin-deficient cells) were tested.

Cy3-labeled PNDA-3 was reacted with periostin-positive cells 4T1 (purchased from ATCC) or periostin-negative cells (MCF7; purchased from ATCC). Each about 0.2×10$^6$ of the two kinds of cells were cultured in 200 uL of selection buffer (200 mM HEPES, 510 mM NaCl, 25 mM KCl, 25 mM MgCl$_2$) together with 100 nM Cy3-labeled PNDA-3 at 4° C. for 1 hours. Thereafter, the cells were washed with 200 uL of selection buffer three times, and resuspended in 500 uL of 4% (w/v) paraformaldehyde (PFA). The prepared sample was analyzed on FL3-H channel of FACSCalibur (BD Biosciences, San Jose, Calif.).

Figure 3A:
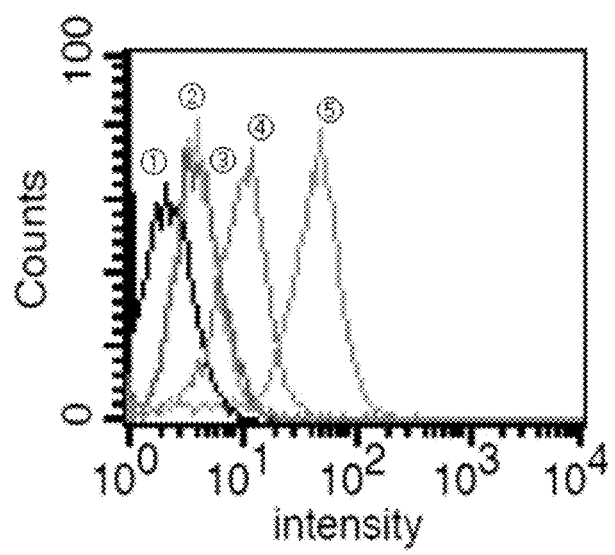
FIG. 3 shows that the PNDA according to one example binds to periostin expressed on the surface of cell and inhibits interaction with integrin, wherein 3A is the results showing aptamer binding to periostin positive cell line 4T1, 3B is the result for periostin negative cell line MCF7, and 3C is the TIR fluorescent microscope result showing that PNDA inhibits interaction of periostin and integrin.
Figure 3B:
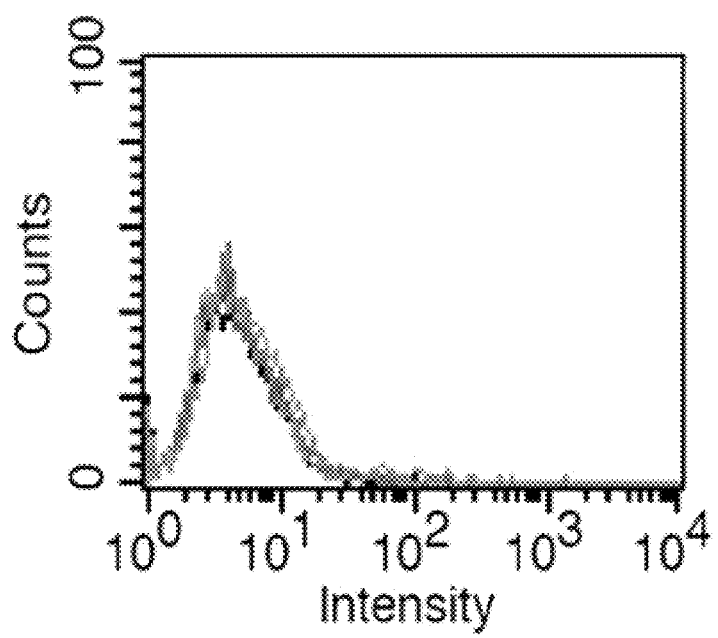

The cells were analyzed by flow cytometry, and as control, cell line was cultured alone. The obtained results are shown in FIGS. 3A (4T1 cells) and 3B (MCF7 cells). As shown in FIG. 3A, although Cy3-labeled PNDA-3 binds to 4T1 cells, control aptamer (CTL) does not bind to cell line (FIG. 3A). And, it was shown that the aptamer of the present invention does not bind to negative control cell line MCF7 cells beyond background level (FIG. 3B). Thus, it was shown that the aptamer PNDA-3 of the present invention can specifically recognize periostin on the surface of cells.

Figure 3C:
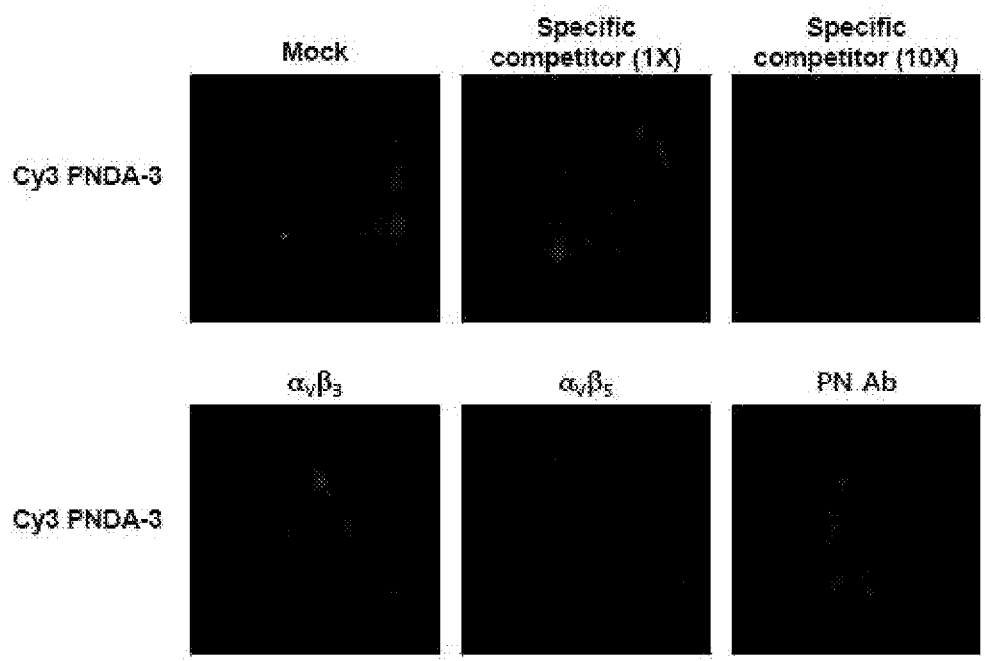

In order to confirm binding of PNDA-3 with the cell surface of periostin, cy3-PNDA-3 binding was observed with TIR (total internal reflection) fluorescent microscope (Cell®, Olympus, final magnification 100×) by the above explained method. After 100 nM Cy-3 PNDA-3 was added to the culture medium of 4T1 cell line, it was confirmed that red fluorescent spots are observed on the cell surface. In FIG. 3C, it is confirmed that binding of PNDA-3 to cell surface is completely inhibited by the addition of excessive amount of non-labeled PNDA-3. And, it can be seen that adding integrin antibody significantly reduced PNDA-3 binding to cell surface. Namely, it is confirmed that PNDA-3 inhibits interaction between periostin and integrin.

Example 4

Mapping of Aptamer Binding Region

Figure 4A:
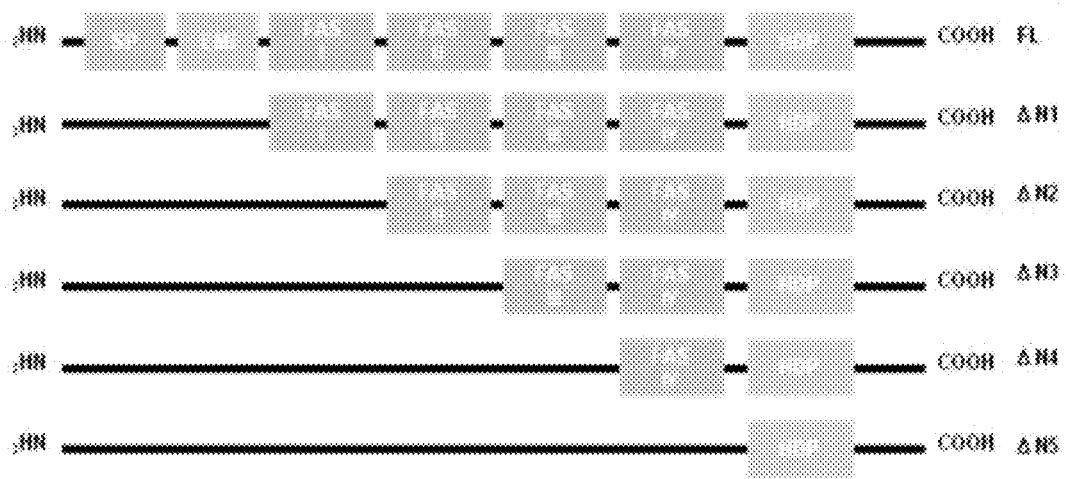
FIGS. 4A and 4B are the results showing that the PNDA according to one example binds to fas-1 domain of periostin.

In order to find the binding region of PNDA-3, mutants shown in FIG. 4A were made through subcloning. The whole length human periostin cDNA used for cloning was supplied from Wang X F, Ph.D. of Duke University. Each mutant was overexpressed in 293T cell line (purchased from ATCC), and then, the cells were dissolved with cell lysis buffer (50 mM HEPES, pH 7.2, 150 mM NaCl, 1 mM EGTA, 1 mM EDTA, 1% Triton X-100, 10% glycerol, 1 mM sodium orthovanadate, 1 mM sodium fluoride, 1 mM phenylmethysulfonyl fluoride, complete protease inhibitor cocktail (Roche)), and centrifuged at 4° C. 14,000×g for 10 minutes. The concentration of protein was measured with Bio-Rad protein assay kit (biorad, #500-0002). The same amount of mutant cell lysates were reacted with 20 pmol of biotin-PNDA-3 at 4° C. for 2 hours, and then, streptavidin bead was added to separate aptamer-protein complex, which was washed with cell lysis buffer 4 times, and then, the bead was eluted with 2× sample buffer, separated in 6-16% SDS-PAGE gel and transferred to nitrocellulose membrane. The membrane was reacted with anti-GFP (santa cruze) antibody at 4° C. for 12 hours. The antibody was detected using corresponding horseradish peroxidase-conjugated secondary antibody (Cell Signaling Technology, Inc). Corresponding protein was detected with ECL kit (Thermo Scientific, Rockford, Ill., USA) and analyzed by ImageQuant™ LAS 4000 (GE Healthcare).

Figure 4B:
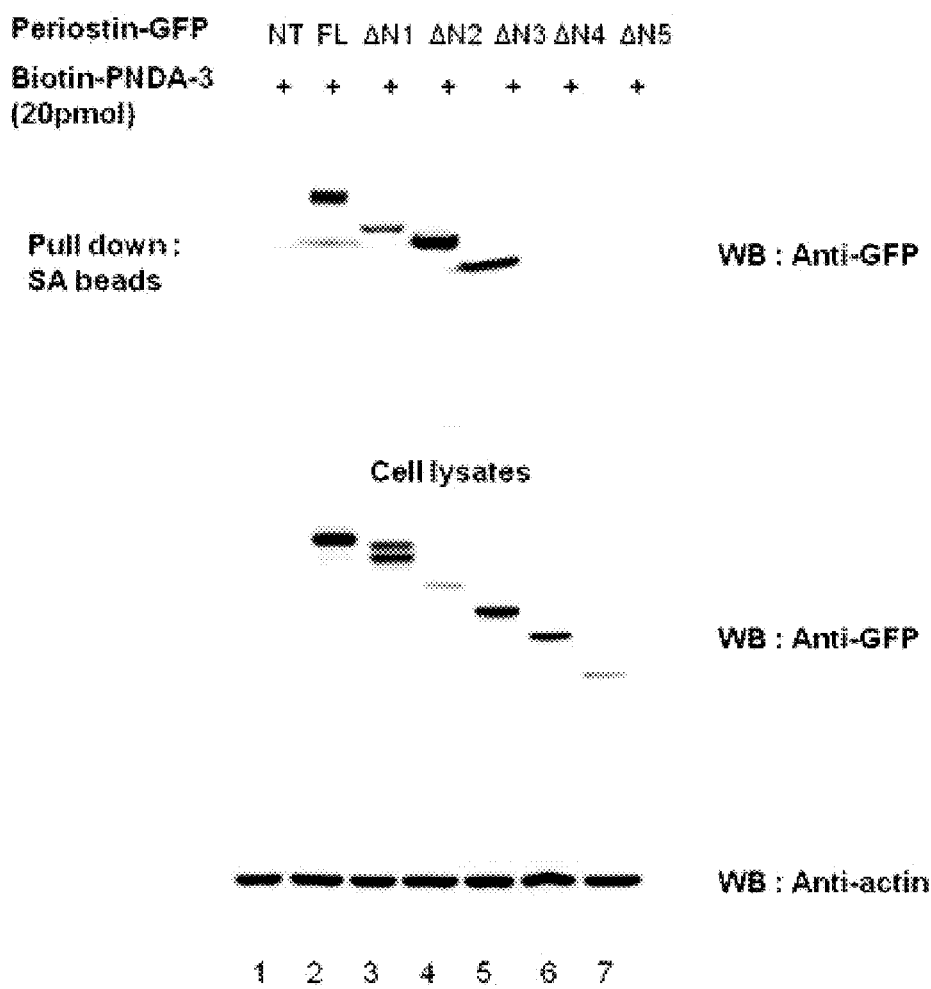

As can be seen from FIG. 4B, although the whole length periostin forms a complex with PNDA-3 and is confirmed by Western blot, the binding is remarkably decreased in mutants 4 and 5. Namely, the important and essential domain for binding of PNDA-3 to periostin is the third fas-1 domain, which is expected to be an important part for binding with integrin.

Example 5

Periostin-Mediated Breast Cancer Cell Adhesion, Migration and Metastasis Inhibition Test (In Vitro)

By in vitro assay for adhesion, migration and metastasis, the effects of periostin and anti-periostin aptamer (PNDA-3) on the possibility of metastasis of several breast cancer cell lines such as MCF7, 4T1, and MDA-MB-231 cells were investigated.

On a 96-well microtiter plate coated with 10 ug/ml type I Collagen (Sigma) or 10 ug/ml periostin, adhesion assay was conducted. To block non-specific binding, the plate was blocked with 0.2% BSA at 37° C. for 1 hour. The cells were treated with trypsin, and suspended in DMEM containing 1% BSA, 1 mM $MgCl_2$, 0.5 mM $CaCl_2$ at a concentration of $1\times10^6$ cells/ml. MCF7, 4T1, and MDA-MB-231 cells (each $1\times10^6$) were exposed to 100 nM aptamer or 2 ug Ab ($\alpha_v\beta_3$ or $\alpha_v\beta_5$ antibody) for 30 minutes. The cells ($1\times10^6$ cells, 100 ul) were added to each well, and subjected to $CO_2$ humidified air incubation of 37° C. for 30 minutes. The well was washed with phosphate-buffered saline (PBS) three times to remove non-adhered cells. The adhered cells were fixed with 4% paraformaldehyde at room temperature for 10 minutes, washed with PBS, and stained with 0.4% crystal violet for 10 minutes. The stained sample was eluted with a 30% acetic acid solution and analyzed at 590 nm with a microplate reader (Molecular Devices, Berkeley, Calif.).

Figure 5A:
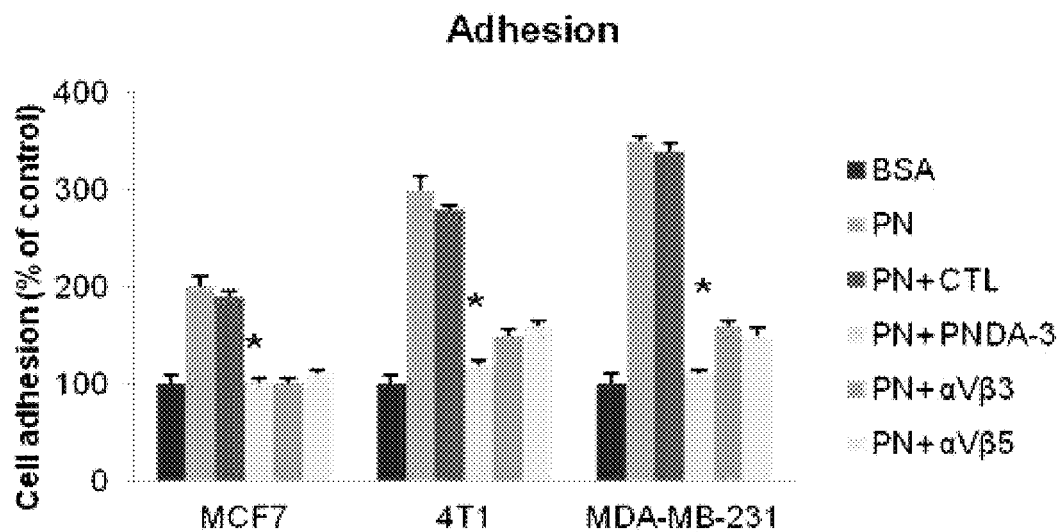
FIG. 5 shows the inhibition effect of the PNDA according to one example for breast cancer cell adhesion, migration and invasion, wherein 5A is the result of cell adhesion assay, 5B is the result showing the effect of PNDA on breast cancer cell migration, 5C is the result of Matrigel invasion assay, and 5D is the result confirming the toxicity of PNDA for breast cancer cell line used in the experiment.

The results are shown in FIG. 5A. As can be seen from FIG. 5A, cell adhesion remarkably (60%) decreased in MDA-MB-231 cells in the presence of anti-periostin aptamer, while non-specific control aptamer (CTL) did not have any influence. By the treatment with anti-$\alpha_v\beta_3$ and $\alpha_v\beta_5$ antibodies, similar degree of breast cancer cell adhesion inhibition was confirmed in periostin-coated well (50% of control, P<0.05).

The migration and invasion assays were conducted in modified Boyden Chamber system (BD falcon, #354578). In the case of migration assay, a porous filter (8 um) was cultured overnight with 20 ug/ml type I Collagen (Sigma) dissolved in 0.1 M acetic acid at 4° C. to conduct coating by passive absorption of type I Collagen. MCF7, 4T1, and MDA-MB-231 cells (each $2\times10^4$) were mixed with 50 uL of serum free medium (DMEM(Lonza)-4T1, MDA-MB-231 cell line; RPMI (Lonza)-MCF7) and added to the upper chamber, and then, allowed to migrate in 37° C. incubator for 4 hours. Periostin (or BSA, 1 ug/mL) or PNDA-3 (or control aptamer, 100 nM) was added to the lower chamber. Migrated cells that were adhered to the lower side of the filter were fixed with 4% PFA, and non-migrated cells were removed with cotton swab. 0.2% Triton X-100 was penetrated into the cell membrane, and then, nucleus was stained with Hoeschest 33342 solution (sigma). The results of cell migration are shown by counting the number of average cells per area of 6 different locations at 10 magnification. The obtained results are shown in FIG. 5B.

Figure 5B:
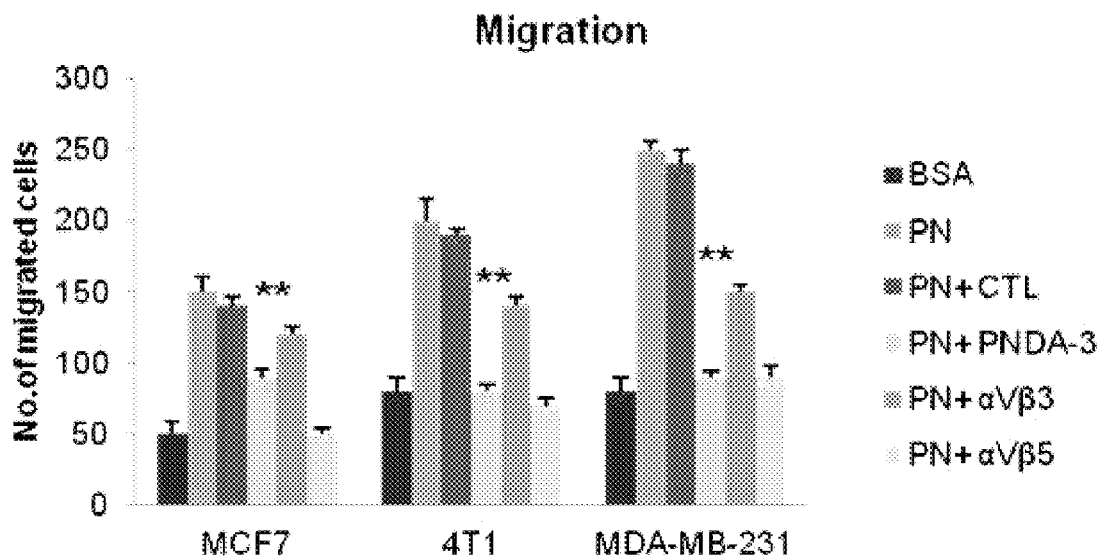

In FIG. 5B, periostin effectively promotes migration capacity of breast cancer cell line, compared to negative control using BSA (MCF7: 3 fold, 4T1: 4 fold, MDA-MB-231: 5 fold). Although the addition of non-specific control aptamer does not significantly influence on the cell migration induced by periostin, PNDA-3 remarkably decreases such reaction (MCF7: 40%, 4T1: 60%, MDA-MB-231: 67%, P<0.05).

In an invasion assay, MCF7, 4T1, and MDA-MB-231 cells lines were put in an internal chamber coated with growth factor reduced Matrigel (BD Biosciences) at $1\times10^5$ cell lines, and after 24 hours, cells reaching the lower chamber were tested by the same method as the cell migration test. The obtained results are shown in FIG. 5C.

Figure 5C:
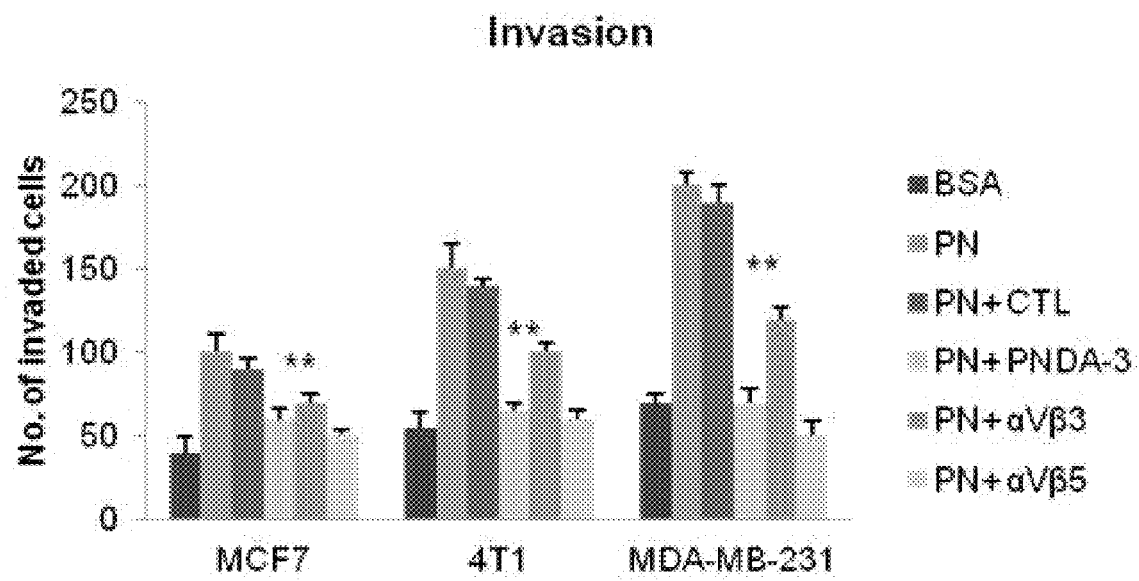

As shown in FIG. 5C, it is confirmed that invasion of breast cancer cell line is increased by periostin, compared to BSA treated control. It can be seen that control aptamer does not influence on the action of periostin, while PNDA-3 significantly inhibits cell invasion of breast cancer cell line (MCF7: 40%, 4T1: 60%, MDA-MB-231 65%). Compared to BSA treated group, integrin $\alpha_v\beta_3$, $\alpha_v\beta_5$ inhibition antibodies-treated groups also inhibit cell invasion induced by periostin to the similar level to the PNDA-3 aptamer treated group. However, the effect of integrin $\alpha_v\beta_3$ inhibition antibody-treated group for inhibiting cell migration and invasion induced by periostin is not significant, compared to integrin $\alpha_v\beta_5$ inhibition antibody-treated group. Thus, it can be seen that integrin $\alpha_v\beta_5$ is the major cell surface factor on which periostin acts in breast cancer cell line.

Figure 5D:
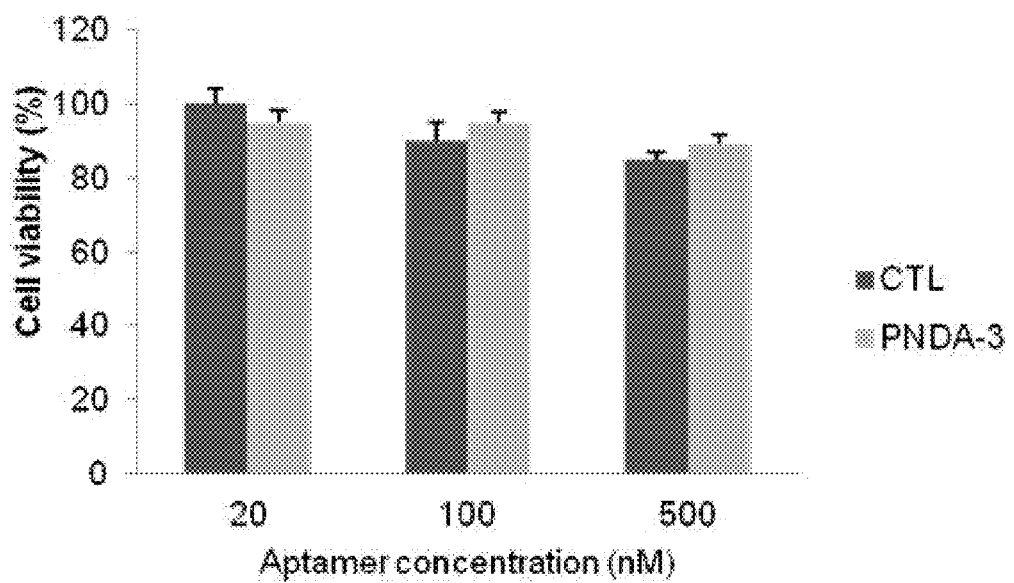

The toxicity of PNDA-3 was confirmed in breast cancer cell line. 4T1 cells ($0.5\times10^4$) were put in a 96-well plate, and allowed to adhere overnight. PNDA-3 was used at various concentrations, at least 6 wells per test corresponding to one concentration were exemplified, and each experiment was repeatedly conducted three times. The cells were treated in 200 ul of DMEM medium together with the indicated concentrations of PNDA-3 (or CTL). To measure cell viability, 10 uL of MTT solution (5 mg/mL, Sigma) was added and cultured for 3 hours. Formazan was dissolved in 50 uL of DMSO and absorbance was measured at 540 nm. The cell viability was shown as the relative value compared to sham-treated control cells in FIG. 5D. As shown in FIG. 5D, even if treated with 500 nM aptamer, there was no remarkable change in cell morphology or cell viability.

Example 6

Signaling Pathway Inhibition Test

Each $3\times10^5$ of breast cancer cell lines (4T1, MDA-MB-231) were seeded in a 6-well plate, cultured in a growth medium (Lonza)+10% FBS(Gibco)+antibiotics(gibco)) for 24 hours, and then, cultured in serum-free medium (DMEM) for 18 hours. Thereafter, they were treated with 100 nM of aptamer and 5 ug of integrin neutralizing antibodies (integrin $\alpha_v\beta_3$ and $\alpha_v\beta_5$ antibodies) for 3 hours. The cells were dissolved with cell lysis buffer (50 mM HEPES, pH 7.2, 150 mM NaCl, 1 mM EGTA, 1 mM EDTA, 1% Triton X-100, 10% glycerol, 1 mM sodium orthovanadate, 1 mM sodium fluoride, 1 mM phenylmethysulfonyl fluoride, complete protease inhibitor cocktail (Roche)), and centrifuged at 4° C. 14,000×g for 10 minutes. The concentration of protein was measured with Bio-Rad protein assay kit (biorad, #500-0002), and the protein sample was separated in 6-16% SDS-PAGE gel and transferred to a nitrocellulose membrane.

The membrane was reacted with the following primary antibodies at 4° C.:

FAK Ab, phospho-FAK Ab (Tyr925) (Cell Signaling, Beverly, Mass.),

Src Ab, phospho-Src Ab (Cell Signaling, Beverly, Mass.), and

β-actin Ab (Santa Cruz Biotechnology, Santa Cruz, Calif.).

These antibodies were detected using corresponding horseradish peroxidase-conjugated secondary antibody (Kirkegaard & Perry Laboratories, KPL, Gaithersburg, Md., USA). Corresponding protein was analyzed with an ECL kit (Thermo Scientific, Rockford, Ill., USA) and visualized with ImageQuant™ LAS 4000 (GE Healthcare).

From the results, it was confirmed that PNDA-3 binds to periostin existing on the cell surface and inhibits binding with integrin, thereby inhibiting metastasis (cell adhesion, migration and invasion) induced by periostin. Next, to examine the influence of PNDA-3 on periostin-dependent signal transduction pathway, immunoblotting was conducted. The phosphorylations of FAK and SRC, which are known as markers of integrin signal transduction pathway and cell spreading, were confirmed and the results are shown in FIG. 6A and FIG. 6B.

Figure 6A:
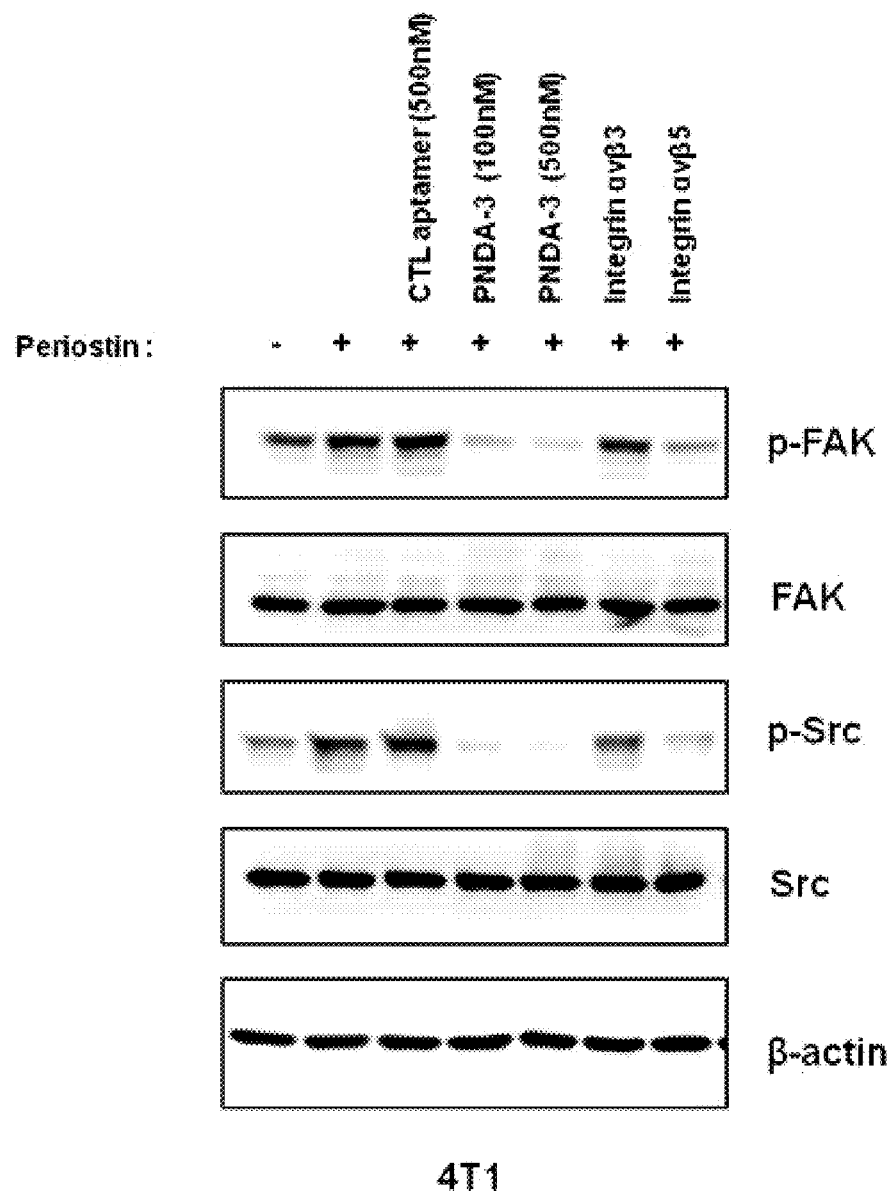
FIG. 6 shows the inhibition of periostin-dependent signal pathway by the PNDA according to one example, wherein 6A is the result in 4T1 cells, and 6B is the result in MDA-MB-231 cells.
Figure 6B:
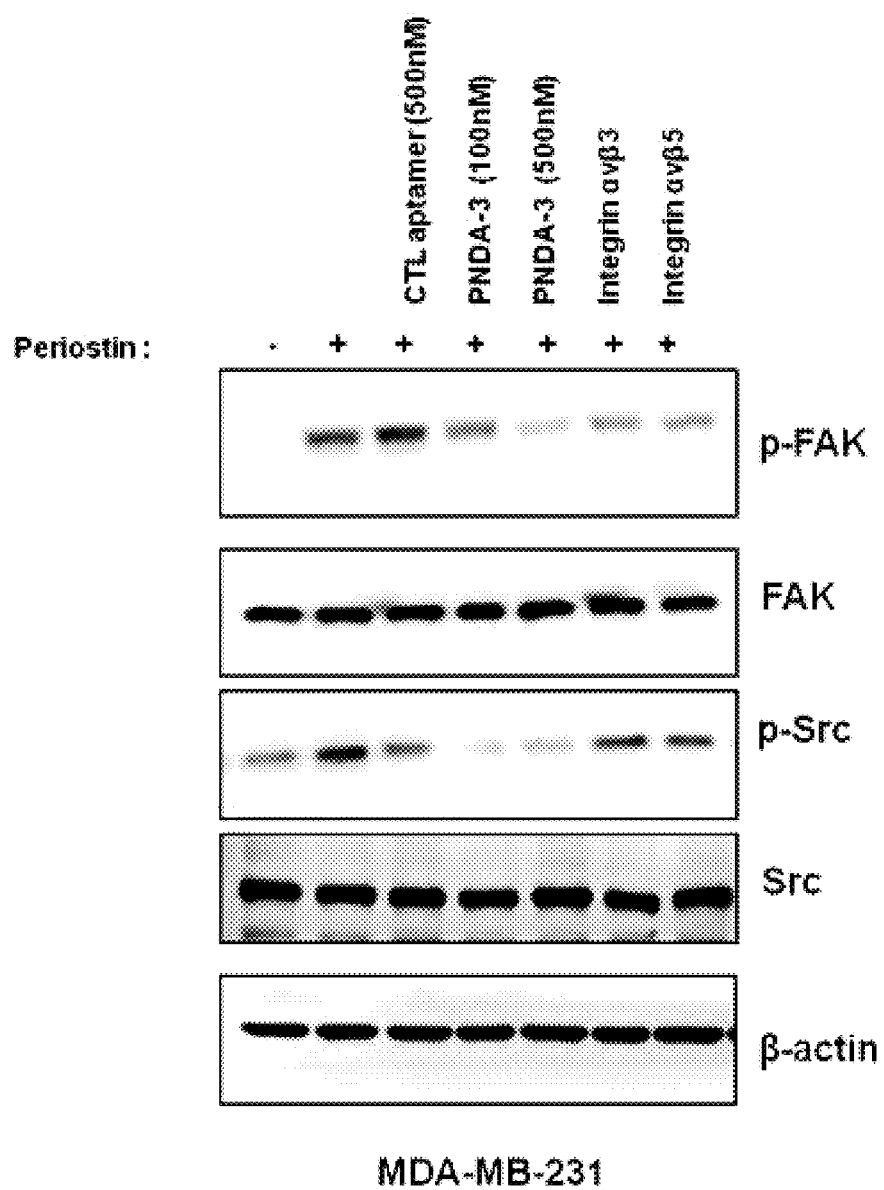
Figure 7:
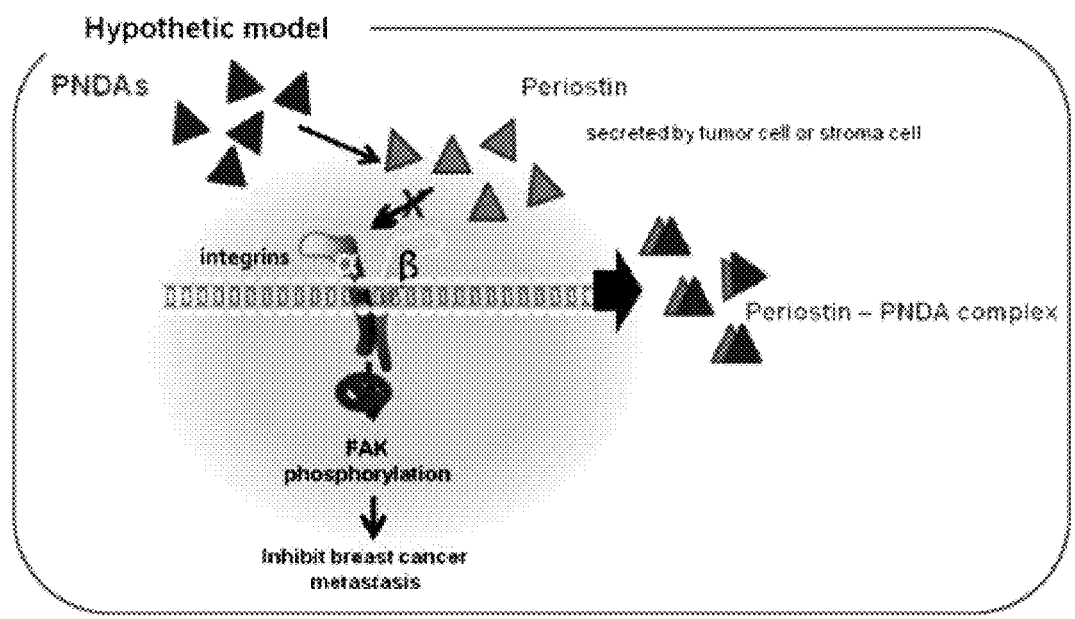
FIG. 7 schematically shows the function of the PNDA according to one example.

As shown in FIGS. 6A and 6B, the western blot analysis revealed increased levels of FAK anad SRC phosphorylation in cells exposed to perisoitn. PNDA-3 or anti-integrin Abs ($α_Vβ$ and $α_Vβ_5$) treatment drastically reduced FAK and Scr phosphorylation levels in 4T1 and MDA-MB-231 cells, whereas no effects were observed in the presence of the control aptamer. Furthermore, the dose-dependent inhibition of FAK and Src phosphorylation was correlated with the PNDA-3 concentration in 4T1 and MDA-MB-231 cells. Based on the results, it can be seen that in breast cancer cell line, the stimulation of integrin sub-signal by periostin occurs through integrin $α_Vβ_5$. Namely, at molecular level, binding of periostin and integrin promotes the activities of FAK and SRC, which consequently activates cell migration and invasion to increase breast cancer metastasis. The aptamer according to one embodiment of the invention has the effect of inhibiting these actions to inhibit breast cancer metastasis.

Example 7

Tumor Growth and Metastasis Inhibition Test (In Vivo)

The anti-tumor growth and metastasis inhibition efficacies of PNDA-3 were tested in an animal model.

6-week-old female BALB/c mice (Charles River Breeding Laboratories) were raised under pathogen-free conditions in animal raising facility of Pohang University of Science and Technology (POSTECH). All the animal test processes followed the regulations of institutional animal care and use committee of POSTECH. Breast cancer cell line 4T1 ($1 \times 10^4$ cells, purchased from ATCC) was suspended in 0.1 mL of Hank's balanced salt solution (HBSS, Gibco) and implanted into the L4 position of mouse mammary fat pads (10 mice per group). 30 non-necrotic tumor models of about 0.5 cm³ size were randomly divided into 3 groups with 10 mice per group as follow:
Group 1: vehicle (HBSS);
Group 2: CTL aptamer treated;
Group 3: PNDA-3 treated.

Control aptamer, PNDA-3 aptamer (500 μg/kg), and vehicle were respectively intratumorally administered into primary tumor at a total volume of 50 μL three times a week for 16 days. During each test, signs of suffering of the mouse was monitored daily. The size of tumor was measured every other day using a caliper, and the volume of tumor (V) was calculated by the following Equation:

$V = (1/2) \times \text{long diameter} \times (\text{short diameter})^2$.

Growth curve was plotted as mean tumor volume±SEM (n=10).

Figure 8A:
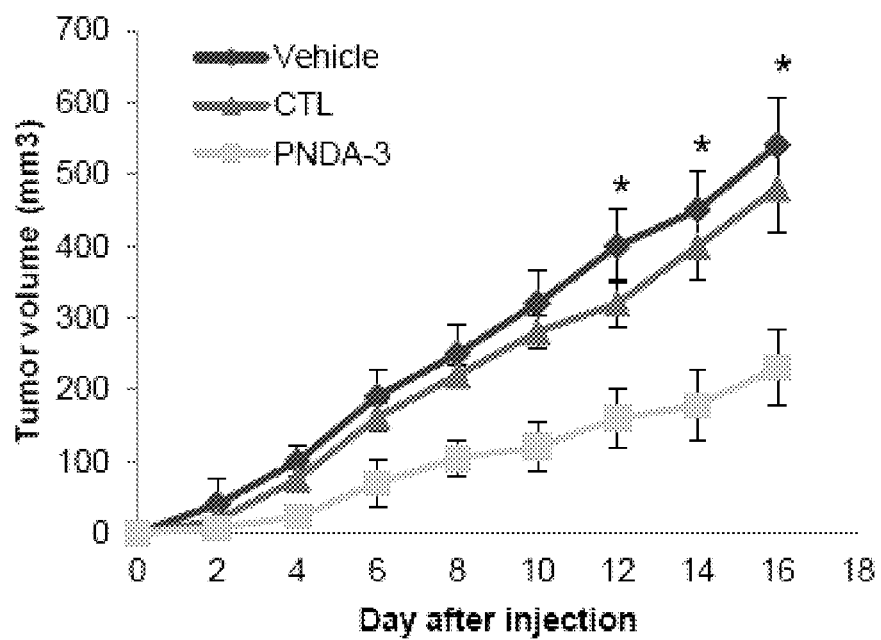
FIG. 8A to 8E show the in vivo result of breast cancer cell growth and metastasis inhibition of the PNDA according to one example, wherein 8A is a graph showing change in tumor size according to PNDA treatment, 8B is a graph showing weight change of a mouse model according to PNDA treatment, 8C is a photograph showing the inhibition of breast cancer metastasis to lung according to PNDA treatment (arrow represents nodules), 8D is a graph quantified the nodules of the lung of 8C, and 8E is a microscope photograph showing the H&E staining of lung tissue according to PNDA treatment.

The obtained results are shown in FIG. 8A. FIG. 8A shows PNDA-3-mediated tumor growth inhibition in a syngeneic breast cancer model having periostin positive 4T1 cells (42% at day 16 compared with CTL or the control group; *, P<0.01 with a Mann-Whitney test). "Day 0" means the first day of injection. The data was shown as "mean±SEM" (n=10 tumors).

Figure 8B:
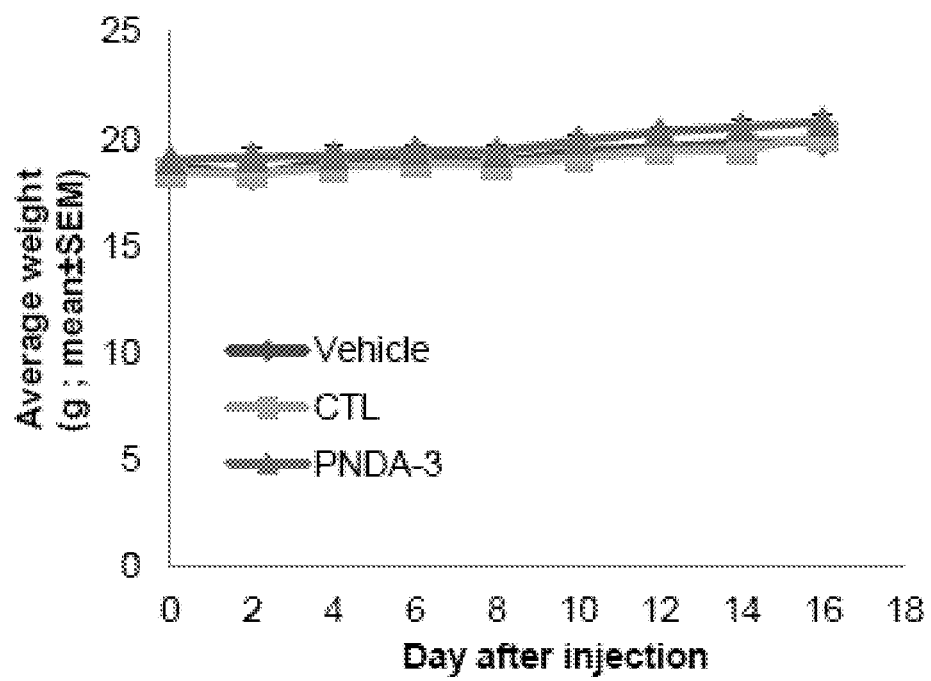

As shown in FIG. 8A, when PNDA-3, control aptamer and vehicle were respectively intratumorally administered into primary tumor three times a week, PNDA-3 treated group showed remarkable decrease in tumor growth compared to control and vehicle administered groups, and particularly, at day 16, tumor size decreased about 58% compared to vehicle treated group (P<0.02). The weights of the three groups were measured and shown in FIG. 8B. As shown in FIG. 8B, there was no difference in body weight decrease between PNDA-3-administered group and control aptamer-administered group, which means that the aptamer does not exhibit toxicity during treatment.

And, at day 20 after administering aptamer, metastasis and the size of primary tumor were measured and shown in the following Table 5.

TABLE 5

Summary of analysis for metastases and primary tumor size in breast cancer mouse model using Balb/C mice.

|  | Vehicle | CTL | PNDA-3 |
| --- | --- | --- | --- |
| Mice with metastases | | | |
| Number | 10/10 | 9/10 | 3/10 |
| Lung | 10/10 | 9/10 | 2/10 |
| Liver | 2/10 | 0/10 | 0/10 |
| Spleen | 5/10 | 3/10 | 1/10 |
| Lymph nodes | 8/10 | 7/10 | 2/10 |
| Primary tumor size, mm³ | | | |
| Mean (95% CI **) | 540 | 480 | 230 |

* Note:
Compared with Vehicle, treatment with PNDA-3 not only significantly reduced tumor burden (P < 0.02), but also decreased tumor lung metastases. P values (two-sided) were calculated using Student's t test.
** CI: confidence interval As shown in Table 5, on day 20 following injection, necropsy tissues revealed a similar tumor distribution in all mice implanted with breast cancer cells, including an extensive tumor mass and distant metastases in the lymph nodes, liver, spleen, and lung. Strikingly, several nodules and larger metastatic foci (≥2 mm) were observed in the lung tissue of the vehicle- and control aptamer-treated groups, whereas PNDA-3 treatment significantly reduced the nodules and metastatic foci (P<0.005)).

Figure 8C:
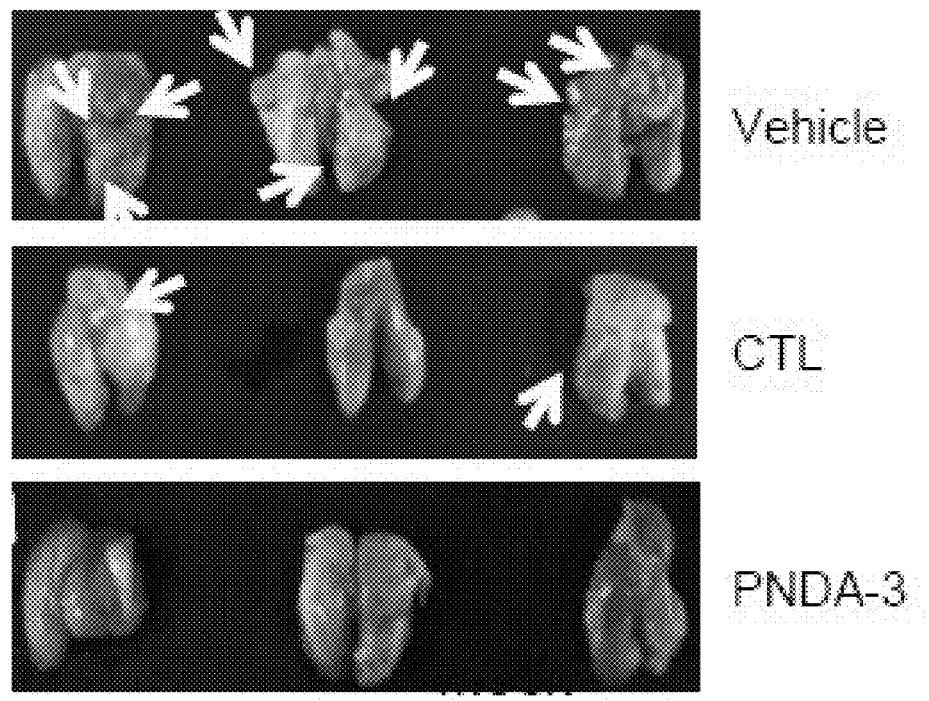
Figure 8D:
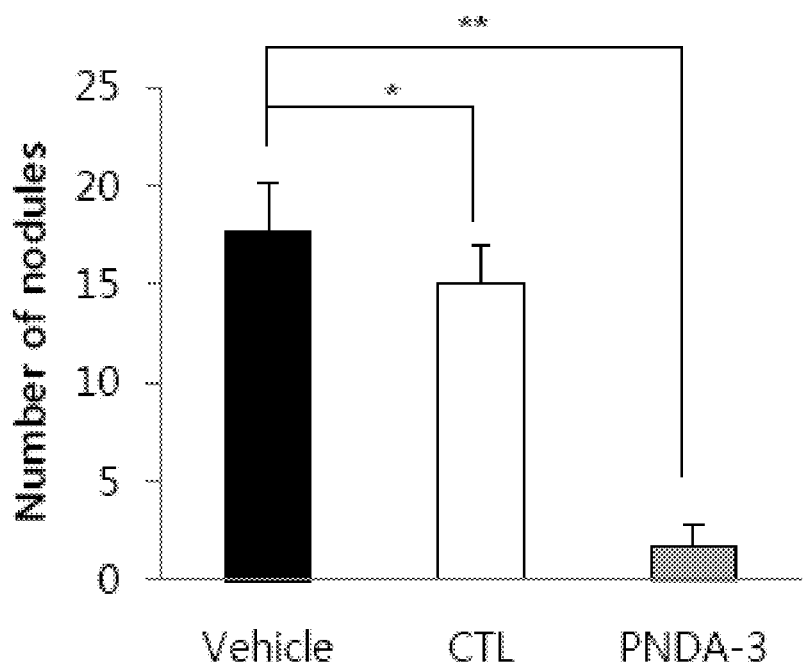
Figure 8E:
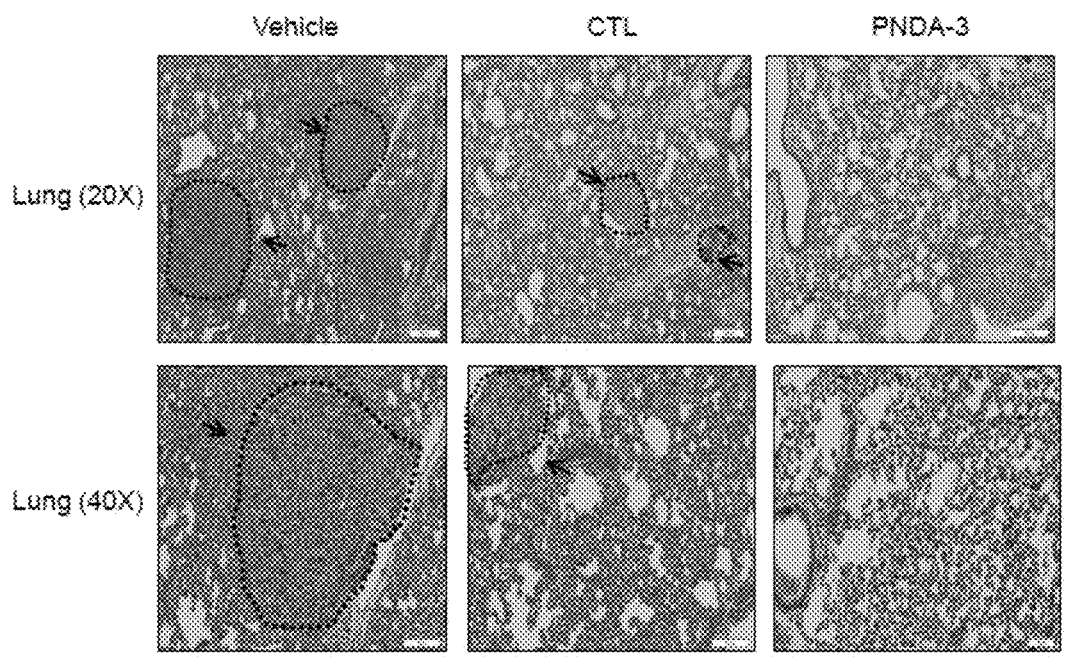

FIGS. 8C and 8D shows the inspection results of aptamer treated group and non-treated group mice, wherein FIG. 8C shows extracted lung (arrow represents lung nodule), and FIG. 8D shows the number of lung nodules by bar graph (n=10; *, P<0.0001; **, P<0.005). And, FIG. 8E shows H&E stained lung tissues, and shows metastatic foci in each group (vehicle treated group, control aptamer treated group, or PNDA-3 aptamer treated group). The arrow and the circle of dotted line represent metastatic foci in lung. Scale bars: 200 μm (top); 100 μm (bottom). In vehicle-treated group and control aptamer-treated group, metastatic foci to several lung tissues were observed, while in PNDA-3 treated group, metastatic foci were remarkably decreased.

Example 8

Histological Test and Immunohistochemical Test

In order to confirm the relationship between tumor growth inhibition by PNDA-3 and inhibition of the function of vascular endothelial cells such as angiogenesis or vascular endothelial cell growth, immunostaining of vascular marker CD31 and cell growth marker Ki-67 was conducted. Paraffin-embedded tumor tissues were sectioned to a thickness of 4 μm. To inhibit endogenous peroxidases, the obtained section was treated with 0.5% (v/v) $H_2O_2$ (in 100% (v/v) methanol) at room temperature for 15 minutes. For histological test, a part of the paraffin section was stained with hematoxylin and eosin (H&E) to confirm tumor diagnosis.

Blood vessel marker (CD31, BD Pharmingen, San Diego, Calif.), Ki-67 (Dako Corporation, CA) and anti-periostin antibody (Abcam) staining were performed to determine whether PNDA-3 inhibits tumor growth by suppressing the occurrence of tumor-associated cells. The prepared section was incubated overnight at 4° C. on a slide together with the primary antibody, and then, the slide was incubated together with biotinylated secondary antibody and peroxidase-labeled streptavidin (Dako), and the peroxidase activity was measured using diaminobenzidine as a chromogenic substrate.

The slide was counter stained with hematoxilin, and mounted using a mounting medium (Dako). The slide was observed with a digital virtual microscope (dotSlide; Olympus, Tokyo, Japan) and MetaMorph image software (Molecular Devices, Sunnyvale, Calif.) and analyzed.

Figure 9A:
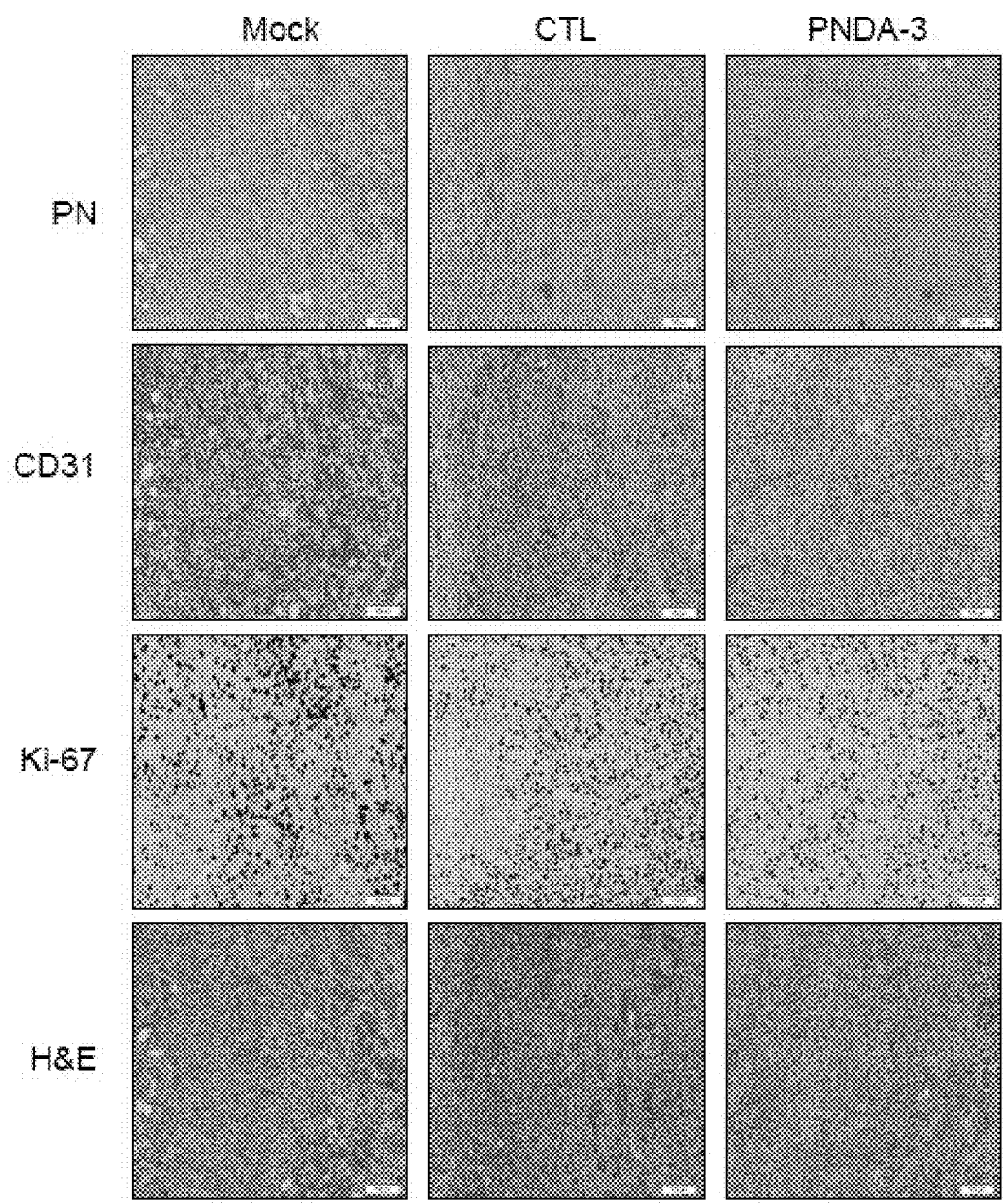
FIGS. 9A to 9C shows in vivo effect of the PNDA according to one example for tumor cell growth and angiogenesis, wherein 9A is a microscope photograph showing the immunostaining result of primary tumor section according to PNDA treatment, and 9B and 9C are graph quantitatively showing the immunohistochemical experiment results using Ki-67 antibody (9B) and CD31 antibody (9C).
Figure 9B:
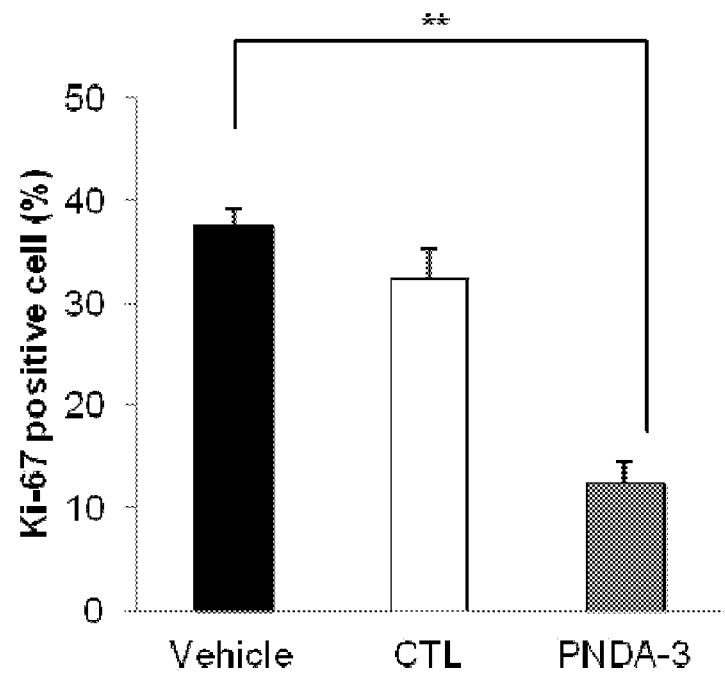
Figure 9C:
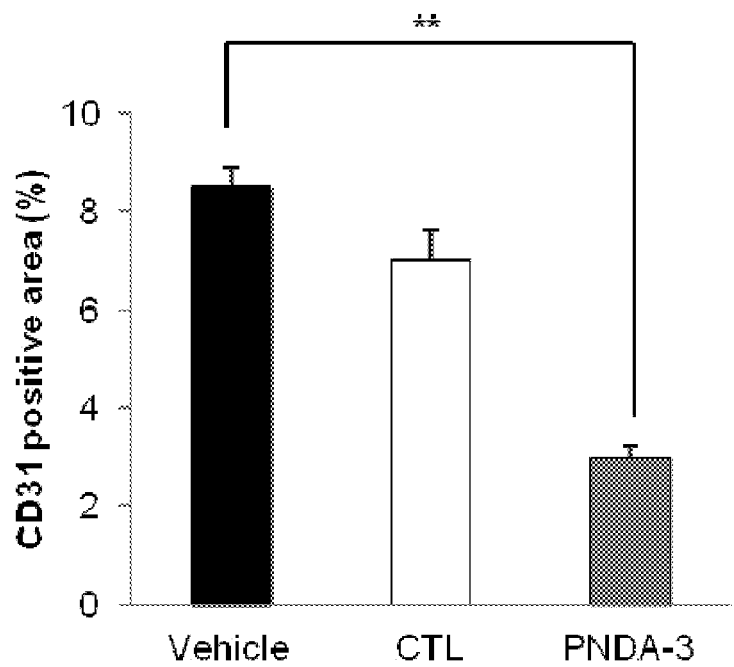

The obtained results are shown in FIGS. 9A-9C. FIG. 9A shows microscope images of the immunostaining results of the primary tumor sections obtained from vehicle treated group, control aptamer treated group and PNDA-3 aptamer treated group. FIGS. 9B and 9C respectively show the results of quantifying Ki-78 (9B) staining and CD31 (9C) staining of proliferated cells and endothelial cells. The percent values represent mean±S.D. for optionally selected 10 fields. *, P<0.05. The circle images were digitally captured. Scale bar: 100 μm.

The tumor obtained in PNDA-3 treated group showed remarkably decreased number of proliferating cells and blood vessels density, compared to vehicle treated group and control aptamer treated group. And, when the tumors were treated with PNDA-3, periostin expression amount (→amount 생략) was decreased compared to control aptamer-treated group and vehicle treated group. In conclusion, PNDA-3 inhibits the progression and metastasis of breast cancer in breast cancer xenographed mouse model, and inhibits angiogenesis at least partly through the inhibition of growth of tumor cells or tumor related cells such as vascular endothelial cells.

Statistical Analysis

All the data were presented as mean±S.D. of at least three times repeated samples. The difference between two groups was analyzed using Student's t-test. P<0.05 was considered as a significant numerical value.

---

SEQUENCE LISTING

```
<160> NUMBER OF SEQ ID NOS: 51

<210> SEQ ID NO 1
<211> LENGTH: 5
<212> TYPE: DNA
<213> ORGANISM: Artificial Sequence
<220> FEATURE:
<223> OTHER INFORMATION: 5'-end sequence 1 of aptamer

<400> SEQUENCE: 1 acgag                                                                       5

<210> SEQ ID NO 2
<211> LENGTH: 5
<212> TYPE: DNA
<213> ORGANISM: Artificial Sequence
<220> FEATURE:
<223> OTHER INFORMATION: 3'-end sequence 1 of aptamer

<400> SEQUENCE: 2 aacaa                                                                       5

<210> SEQ ID NO 3
<211> LENGTH: 19
<212> TYPE: DNA
<213> ORGANISM: Artificial Sequence
<220> FEATURE:
<223> OTHER INFORMATION: 5'-end sequence 2 of aptamer

<400> SEQUENCE: 3
gatgtgagtg tgtgacgag                                                       19

<210> SEQ ID NO 4
<211> LENGTH: 20
<212> TYPE: DNA
```

```
<213> ORGANISM: Artificial Sequence
<220> FEATURE:
<223> OTHER INFORMATION: 3'-end sequence 2 of aptamer

<400> SEQUENCE: 4
aacaacagaa caaggaaagg                                              20

<210> SEQ ID NO 5
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl,
      and/or tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with  benzyl, naphthyl, pyrrolebenzyl, and/o
   r tryptophan
<220> FEATURE:
<221> NAME/KEY: misc_feature
<222> LOCATION: (9)..(10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (13)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (17)..(18)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (25)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (27)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
```

```
<222> LOCATION: (30)..(31)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (35)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (37)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (40)
<223> OTHER INFORMATION: n is 'T' or a modified dU in which 5-position
      is substituted with benzyl, naphthyl, pyrrolebenzyl, and/or
      tryptophan

<400> SEQUENCE: 5
ncnggnccnn ccngnannag ancananccn naggnancgn c                     41

<210> SEQ ID NO 6
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (8)..(9)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (12)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (20)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (23)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (26)..(27)
<223> OTHER INFORMATION: n is 'T' or a modified dU in which 5-position
      is substituted with benzyl, naphthyl, pyrrolebenzyl, and/or
      tryptophan
<220> FEATURE:
```

```
<221> NAME/KEY: misc_feature
<222> LOCATION: (36)
<223> OTHER INFORMATION: n is 'T' or a modified dU in which 5-position
      is substituted with benzyl, naphthyl, pyrrolebenzyl, and/or
      tryptophan

<400> SEQUENCE: 6
ncacacgnng angacnggan ggnagnnaaa gagggngggg c                          41

<210> SEQ ID NO 7
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (13)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (17)..(18)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (25)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (27)
<223> OTHER INFORMATION: n is 'T' or a modified dU in which 5-position
      is substituted with benzyl, naphthyl, pyrrolebenzyl, and/or
      tryptophan
```

```
<220> FEATURE:
<221> NAME/KEY: misc_feature
<222> LOCATION: (29)..(30)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (35)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (37)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (40)
<223> OTHER INFORMATION: n is 'T' or a modified dU in which 5-position
      is substituted with benzyl, naphthyl, pyrrolebenzyl, and/or
      tryptophan

<400> SEQUENCE: 7
ncnganccnn ccngnannag ancanancnn caggnancgn c                          41

<210> SEQ ID NO 8
<211> LENGTH: 42
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(10)
<223> OTHER INFORMATION: n is 'T' or a modified dU in which 5-position
      is substituted with benzyl, naphthyl, pyrrolebenzyl, and/or
      tryptophanhan
<220> FEATURE:
<221> NAME/KEY: misc_feature
<222> LOCATION: (13)..(15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (24)..(25)
<223> OTHER INFORMATION: n is 'T' or a modified dU in which 5-position
      is substituted with benzyl, naphthyl, pyrrolebenzyl, and/or
``` tryptophan
<220> FEATURE:
<221> NAME/KEY: misc_feature
<222> LOCATION: (27)..(29)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (32)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (34)
<223> OTHER INFORMATION: n is 'T' or a modified dU in which 5-position
      is substituted with benzyl, naphthyl, pyrrolebenzyl, and/or
      tryptophan

<400> SEQUENCE: 8
ncnggnccnn ccnnngacga cnanngnnng gnancggaca ac                          42

<210> SEQ ID NO 9
<211> LENGTH: 42
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (13)..(15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (24)..(25)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (27)..(29)
<223> OTHER INFORMATION: n is 'T' or a modified dU in which 5-position is substituted with benzyl, naphthyl, pyrrolebenzyl, and/or
tryptophan
<220> FEATURE:
<221> NAME/KEY: misc_feature
<222> LOCATION: (32)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (34)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (38)
<223> OTHER INFORMATION: n is 'T' or a modified dU in which 5-position
is substituted with benzyl, naphthyl, pyrrolebenzyl, and/or
tryptophan

<400> SEQUENCE: 9
ncnggnccnn ccnnngacga cnanngnnng gnancggnca ac                            42

<210> SEQ ID NO 10
<211> LENGTH: 41
<212> TYPE: DNA
<213> ORGANISM: Artificial Sequence
<220> FEATURE:
<223> OTHER INFORMATION: core sequence of periostin aptamer, wherein n
is 'T' or a modified dU in which 5-position is substituted with
benzyl, naphthyl, pyrrolebenzyl, and/or tryptophan
<220> FEATURE:
<221> NAME/KEY: misc_feature
<222> LOCATION: (1)..(2)
<223> OTHER INFORMATION: core sequence of periostin aptamer, wherein n
is 'T' or a modified dU in which 5-position is substituted with
benzyl, naphthyl, pyrrolebenzyl, and/or tryptophan
<220> FEATURE:
<221> NAME/KEY: misc_feature
<222> LOCATION: (4)
<223> OTHER INFORMATION: core sequence of periostin aptamer, wherein n
is 'T' or a modified dU in which 5-position is substituted with
benzyl, naphthyl, pyrrolebenzyl, and/or tryptophan
<220> FEATURE:
<221> NAME/KEY: misc_feature
<222> LOCATION: (9)
<223> OTHER INFORMATION: core sequence of periostin aptamer, wherein n
is 'T' or a modified dU in which 5-position is substituted with
benzyl, naphthyl, pyrrolebenzyl, and/or tryptophan
<220> FEATURE:
<221> NAME/KEY: misc_feature
<222> LOCATION: (11)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (16)..(17)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (21)
<223> OTHER INFORMATION: core sequence of periostin aptamer, wherein n
is 'T' or a modified dU in which 5-position is substituted with
benzyl, naphthyl, pyrrolebenzyl, and/or tryptophan
<220> FEATURE:
<221> NAME/KEY: misc_feature
<222> LOCATION: (23)
<223> OTHER INFORMATION: core sequence of periostin aptamer, wherein n
is 'T' or a modified dU in which 5-position is substituted with
benzyl, naphthyl, pyrrolebenzyl, and/or tryptophan
<220> FEATURE:
<221> NAME/KEY: misc_feature
<222> LOCATION: (26)

<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (29)..(30)
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (39)
<223> OTHER INFORMATION: core sequence of periostin aptamer, wherein n
      is 'T' or a modified dU in which 5-position is substituted with
      benzyl, naphthyl, pyrrolebenzyl, and/or tryptophan

<400> SEQUENCE: 10
nngncgcang ngcggnncag ncnggnccnn cagcaccgna c       41

<210> SEQ ID NO 11
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (17)..(18)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (25)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature

```
<222> LOCATION: (27)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (30)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (35)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (37)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (40)
<223> OTHER INFORMATION: n is 'T' or a modified dU in which 5-position
      is substituted with benzyl, naphthyl, pyrrolebenzyl, and/or
      tryptophan

<400> SEQUENCE: 11
ncnggnccnn cccanannag ancananccn cgggnancgn c                    41

<210> SEQ ID NO 12
<211> LENGTH: 40
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(11)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)..(17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (19)..(20)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (27)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (32)
<223> OTHER INFORMATION: n is 'T' or a modified dU in which 5-position
      is substituted with benzyl, naphthyl, pyrrolebenzyl, and/or
      tryptophan
<220> FEATURE:
```

<221> NAME/KEY: misc_feature
<222> LOCATION: (35)
<223> OTHER INFORMATION: n is 'T' or a modified dU in which 5-position
      is substituted with benzyl, naphthyl, pyrrolebenzyl, and/or
      tryptophan

<400> SEQUENCE: 12
ccngcgcgnn ncaannnann cccacanacc cncanaagcc                                40

<210> SEQ ID NO 13
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)..(2)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (4)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (11)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)..(17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (21)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (23)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (29)..(30)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (39)
<223> OTHER INFORMATION: n is 'T' or a modified dU in which 5-position
      is substituted with benzyl, naphthyl, pyrrolebenzyl, and/or
      tryptophan

<400> SEQUENCE: 13
nngncgcang ngcggnncag ncnggnccnn cagcaccgng c    41

<210> SEQ ID NO 14
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)..(2)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (4)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (10)..(12)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (21)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (25)..(26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (28)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (32)
<223> OTHER INFORMATION: n is 'T' or a modified dU in which 5-position
      is substituted with benzyl, naphthyl, pyrrolebenzyl, and/or
      tryptophan

<400> SEQUENCE: 14
nngncgaaan nnggnangag naggnngnag gnagagcccg c    41

<210> SEQ ID NO 15
<211> LENGTH: 41
<212> TYPE: DNA
<213> ORGANISM: Artificial Sequence
<220> FEATURE:

```
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (13)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (17)..(18)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (25)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (27)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (30)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (35)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (37)
<223> OTHER INFORMATION: n is 'T' or a modified dU in which 5-position
``` is substituted with benzyl, naphthyl, pyrrolebenzyl, and/or
       tryptophan
<220> FEATURE:
<221> NAME/KEY: misc_feature
<222> LOCATION: (40)
<223> OTHER INFORMATION: n is 'T' or a modified dU in which 5-position
       is substituted with benzyl, naphthyl, pyrrolebenzyl, and/or
       tryptophan

<400> SEQUENCE: 15
ncnggnccnn ccngnannag ancananccn caggnancgn c                    41

<210> SEQ ID NO 16
<211> LENGTH: 42
<212> TYPE: DNA
<213> ORGANISM: Artificial Sequence
<220> FEATURE:
<223> OTHER INFORMATION: core sequence of periostin aptamer, wherein n
       is 'T' or a modified dU in which 5-position is substituted with
       benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
       is substituted with benzyl, naphthyl, pyrrolebenzyl, and/or
       tryptophan
<220> FEATURE:
<221> NAME/KEY: misc_feature
<222> LOCATION: (3)
<223> OTHER INFORMATION: n is 'T' or a modified dU in which 5-position
       is substituted with benzyl, naphthyl, pyrrolebenzyl, and/or
       tryptophan
<220> FEATURE:
<221> NAME/KEY: misc_feature
<222> LOCATION: (6)
<223> OTHER INFORMATION: n is 'T' or a modified dU in which 5-position
       is substituted with benzyl, naphthyl, pyrrolebenzyl, and/or
       tryptophan
<220> FEATURE:
<221> NAME/KEY: misc_feature
<222> LOCATION: (9)..(10)
<223> OTHER INFORMATION: n is 'T' or a modified dU in which 5-position
       is substituted with benzyl, naphthyl, pyrrolebenzyl, and/or
       tryptophan
<220> FEATURE:
<221> NAME/KEY: misc_feature
<222> LOCATION: (13)..(15)
<223> OTHER INFORMATION: n is 'T' or a modified dU in which 5-position
       is substituted with benzyl, naphthyl, pyrrolebenzyl, and/or
       tryptophan
<220> FEATURE:
<221> NAME/KEY: misc_feature
<222> LOCATION: (19)
<223> OTHER INFORMATION: n is 'T' or a modified dU in which 5-position
       is substituted with benzyl, naphthyl, pyrrolebenzyl, and/or
       tryptophan
<220> FEATURE:
<221> NAME/KEY: misc_feature
<222> LOCATION: (22)
<223> OTHER INFORMATION: n is 'T' or a modified dU in which 5-position
       is substituted with benzyl, naphthyl, pyrrolebenzyl, and/or
       tryptophan
<220> FEATURE:
<221> NAME/KEY: misc_feature
<222> LOCATION: (24)..(25)
<223> OTHER INFORMATION: n is 'T' or a modified dU in which 5-position
       is substituted with benzyl, naphthyl, pyrrolebenzyl, and/or
       tryptophan
<220> FEATURE:
<221> NAME/KEY: misc_feature
<222> LOCATION: (27)..(29)
<223> OTHER INFORMATION: n is 'T' or a modified dU in which 5-position
       is substituted with benzyl, naphthyl, pyrrolebenzyl, and/or
       tryptophan
<220> FEATURE:
<221> NAME/KEY: misc_feature
<222> LOCATION: (32)

<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (34)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (38)
<223> OTHER INFORMATION: n is 'T' or a modified dU in which 5-position
      is substituted with benzyl, naphthyl, pyrrolebenzyl, and/or
      tryptophan

<400> SEQUENCE: 16
ncnggnccnn ccnnngacna cnanngnnng gnancggnca ac                          42

<210> SEQ ID NO 17
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_structure
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure
<222> LOCATION: (9)..(10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure
<222> LOCATION: (13)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure
<222> LOCATION: (17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure
<222> LOCATION: (20)..(21)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure
<222> LOCATION: (24)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure

```
<222> LOCATION: (26)..(27)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure
<222> LOCATION: (32)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure
<222> LOCATION: (34)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_structure
<222> LOCATION: (39)
<223> OTHER INFORMATION: n is 'T' or a modified dU in which 5-position
      is substituted with benzyl, naphthyl, pyrrolebenzyl, and/or
      tryptophan

<400> SEQUENCE: 17
ncnggnccnn ccncccnaan ngcngnngag gnancggcna c                     41

<210> SEQ ID NO 18
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (8)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (11)..(13)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (20)..(22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (24)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (27)
<223> OTHER INFORMATION: n is 'T' or a modified dU in which 5-position
      is substituted with benzyl, naphthyl, pyrrolebenzyl, and/or
      tryptophan
<220> FEATURE:
```

<221> NAME/KEY: misc_feature
<222> LOCATION: (29)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (33)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (36)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (39)
<223> OTHER INFORMATION: n is 'T' or a modified dU in which 5-position
      is substituted with benzyl, naphthyl, pyrrolebenzyl, and/or
      tryptophan

<400> SEQUENCE: 18
nccggncnga nnnccaacan nngnccnanc ccngancgnc c                              41

<210> SEQ ID NO 19
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (13)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (20)..(21)
<223> OTHER INFORMATION: n is 'T' or a modified dU in which 5-position
      is substituted with benzyl, naphthyl, pyrrolebenzyl, and/or
      tryptophan <220> FEATURE:
<221> NAME/KEY: misc_feature
<222> LOCATION: (24)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (26)..(27)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (32)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (34)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (39)
<223> OTHER INFORMATION: n is 'T' or a modified dU in which 5-position
     is substituted with benzyl, naphthyl, pyrrolebenzyl, and/or
     tryptophan

<400> SEQUENCE: 19
ncnganccnn ccncccnaan ngcngnngag gnancggcna c              41

<210> SEQ ID NO 20
<211> LENGTH: 41
<212> TYPE: DNA
<213> ORGANISM: Artificial Sequence
<220> FEATURE:
<223> OTHER INFORMATION: core sequence of periostin aptamer, wherein n
     is 'T' or a modified dU in which 5-position is substituted with
     benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (3)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (6)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (9)..(10)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (13)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (15)..(17)
<223> OTHER INFORMATION: n is 'T' or a modified dU in which 5-position
     is substituted with benzyl, naphthyl, pyrrolebenzyl, and/or

```
        tryptophan
<220> FEATURE:
<221> NAME/KEY: misc_feature
<222> LOCATION: (19)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (31)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (33)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (36)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (38)
<223> OTHER INFORMATION: n is 'T' or a modified dU in which 5-position
      is substituted with benzyl, naphthyl, pyrrolebenzyl, and/or
      tryptophan

<400> SEQUENCE: 20
ncnggnccnn ccncnnngnc cccganaggg nanggnancg c                    41

<210> SEQ ID NO 21
<211> LENGTH: 42
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (8)..(9)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (12)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (20)
<223> OTHER INFORMATION: n is 'T' or a modified dU in which 5-position
``` is substituted with benzyl, naphthyl, pyrrolebenzyl, and/or
tryptophan
<220> FEATURE:
<221> NAME/KEY: misc_feature
<222> LOCATION: (23)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (26)..(27)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (36)
<223> OTHER INFORMATION: n is 'T' or a modified dU in which 5-position
is substituted with benzyl, naphthyl, pyrrolebenzyl, and/or
tryptophan

<400> SEQUENCE: 21
ncacacgnng angacnggan ggnagnnaaa gagggngggg gc                42

<210> SEQ ID NO 22
<211> LENGTH: 41
<212> TYPE: DNA
<213> ORGANISM: Artificial Sequence
<220> FEATURE:
<223> OTHER INFORMATION: core sequence of periostin aptamer, wherein n
is 'T' or a modified dU in which 5-position is substituted with
benzyl, naphthyl, pyrrolebenzyl, and/or tryptophan
<220> FEATURE:
<221> NAME/KEY: misc_feature
<222> LOCATION: (3)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (5)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (8)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (11)..(12)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (17)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (19)..(20)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (23)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (25)

<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (28)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (35)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (39)
<223> OTHER INFORMATION: n is 'T' or a modified dU in which 5-position
      is substituted with benzyl, naphthyl, pyrrolebenzyl, and/or
      tryptophan

<400> SEQUENCE: 22
ggncnggncc nnaagangnn cgnancgnac gagcncccna c                          41

<210> SEQ ID NO 23
<211> LENGTH: 39
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (13)..(15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (24)..(25)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (27)..(29)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (32)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (34)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (38)
<223> OTHER INFORMATION: n is 'T' or a modified dU in which 5-position
      is substituted with benzyl, naphthyl, pyrrolebenzyl, and/or
      tryptophan

<400> SEQUENCE: 23
ncnggnccnn ccnnngacga cnanngnnng gnancggnc                               39

<210> SEQ ID NO 24
<211> LENGTH: 39
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)..(17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (26)..(27)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (34)
<223> OTHER INFORMATION: n is 'T' or a modified dU in which 5-position
      is substituted with benzyl, naphthyl, pyrrolebenzyl, and/or
      tryptophan

<400> SEQUENCE: 24
gcgacngggc gaggcnnggg angggnnacg ccgngcagc                               39

<210> SEQ ID NO 25
<211> LENGTH: 49
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with benzyl, naphthyl, pyrrolebenzyl, and/or tryptophan
<220> FEATURE:
<221> NAME/KEY: misc_feature
<222> LOCATION: (5)..(6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (12)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (18)..(19)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (30)..(32)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (36)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (38)
<223> OTHER INFORMATION: n is 'T' or a modified dU in which 5-position
      is substituted with benzyl, naphthyl, pyrrolebenzyl, and/or
      tryptophan

<400> SEQUENCE: 25
aagcnncggn cnggnccnnc ccccncnggcn nnggcncnaa ggggccgcc            49

<210> SEQ ID NO 26
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (11)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (18)
<223> OTHER INFORMATION: n is 'T' or a modified dU in which 5-position is substituted with benzyl, naphthyl, pyrrolebenzyl, and/or
      tryptophan
<220> FEATURE:
<221> NAME/KEY: misc_feature
<222> LOCATION: (20)..(21)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (25)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (28)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (31)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (39)
<223> OTHER INFORMATION: n is 'T' or a modified dU in which 5-position
      is substituted with benzyl, naphthyl, pyrrolebenzyl, and/or
      tryptophan

<400> SEQUENCE: 26
aaggcacacc ncgcacangn naacnacnac ngacacacnc c                          41

<210> SEQ ID NO 27
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)..(2)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (4)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (11)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)..(17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (21)

```
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (23)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (29)..(30)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (39)
<223> OTHER INFORMATION: n is 'T' or a modified dU in which 5-position
      is substituted with benzyl, naphthyl, pyrrolebenzyl, and/or
      tryptophan

<400> SEQUENCE: 27
nngncacang ngcggnncag ncnggnccnn ccgcaccgna c                     41

<210> SEQ ID NO 28
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)..(2)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (4)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (11)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)..(17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (21)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
```

```
<222> LOCATION: (23)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (29)..(30)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (39)
<223> OTHER INFORMATION: n is 'T' or a modified dU in which 5-position
      is substituted with benzyl, naphthyl, pyrrolebenzyl, and/or
      tryptophan

<400> SEQUENCE: 28
nnancacang ngcggnncag ncnggnccnn cagcaccgng c                           41

<210> SEQ ID NO 29
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (2)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (4)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (12)..(13)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (20)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (27)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (32)
<223> OTHER INFORMATION: n is 'T' or a modified dU in which 5-position
      is substituted with benzyl, naphthyl, pyrrolebenzyl, and/or
      tryptophan
<220> FEATURE:
```

<221> NAME/KEY: misc_feature
<222> LOCATION: (37)
<223> OTHER INFORMATION: n is 'T' or a modified dU in which 5-position
     is substituted with benzyl, naphthyl, pyrrolebenzyl, and/or
     tryptophan

<400> SEQUENCE: 29
cnanaaacnc gnngcccccn cacagcngca anacacncgg c          41

<210> SEQ ID NO 30
<211> LENGTH: 50
<212> TYPE: DNA
<213> ORGANISM: Artificial Sequence
<220> FEATURE:
<223> OTHER INFORMATION: core sequence of periostin aptamer, wherein n
     is 'T' or a modified dU in which 5-position is substituted with
     benzyl, naphthyl, pyrrolebenzyl, and/or tryptophan
<220> FEATURE:
<221> NAME/KEY: misc_feature
<222> LOCATION: (5)..(6)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (10)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (12)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (15)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (18)..(19)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (26)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (30)..(32)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (36)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (38)
<223> OTHER INFORMATION: n is 'T' or a modified dU in which 5-position
     is substituted with benzyl, naphthyl, pyrrolebenzyl, and/or
     tryptophan
<220> FEATURE:
<221> NAME/KEY: misc_feature
<222> LOCATION: (50)
<223> OTHER INFORMATION: n is 'T' or a modified dU in which 5-position
     is substituted with benzyl, naphthyl, pyrrolebenzyl, and/or
     tryptophan

<400> SEQUENCE: 30
aagcnncggn cnggnccnnc ccccnggcn nnggcncnaa gggggccgcn        50

<210> SEQ ID NO 31
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (7)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(12)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (14)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (19)..(21)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (24)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (26)..(28)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (37)..(38)
<223> OTHER INFORMATION: n is 'T' or a modified dU in which 5-position
      is substituted with benzyl, naphthyl, pyrrolebenzyl, and/or
      tryptophan

<400> SEQUENCE: 31
ngnaagngnn nncnancann naangnnngc agaccgnnga c        41

```
<210> SEQ ID NO 32
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (5)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (7)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(14)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (19)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (21)..(22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (25)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (28)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (34)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (36)
<223> OTHER INFORMATION: n is 'T' or a modified dU in which 5-position
``` is substituted with benzyl, naphthyl, pyrrolebenzyl, and/or
        tryptophan
<220> FEATURE:
<221> NAME/KEY: misc_feature
<222> LOCATION: (38)..(39)
<223> OTHER INFORMATION: n is 'T' or a modified dU in which 5-position
        is substituted with benzyl, naphthyl, pyrrolebenzyl, and/or
        tryptophan

<400> SEQUENCE: 32
ngngngngnn nnnngnggnc nnaancangc agcngngnng c                            41

<210> SEQ ID NO 33
<211> LENGTH: 42
<212> TYPE: DNA
<213> ORGANISM: Artificial Sequence
<220> FEATURE:
<223> OTHER INFORMATION: core sequence of periostin aptamer, wherein n
        is 'T' or a modified dU in which 5-position is substituted with
        benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
        is substituted with benzyl, naphthyl, pyrrolebenzyl, and/or
        tryptophan
<220> FEATURE:
<221> NAME/KEY: misc_feature
<222> LOCATION: (3)
<223> OTHER INFORMATION: n is 'T' or a modified dU in which 5-position
        is substituted with benzyl, naphthyl, pyrrolebenzyl, and/or
        tryptophan
<220> FEATURE:
<221> NAME/KEY: misc_feature
<222> LOCATION: (6)
<223> OTHER INFORMATION: n is 'T' or a modified dU in which 5-position
        is substituted with benzyl, naphthyl, pyrrolebenzyl, and/or
        tryptophan
<220> FEATURE:
<221> NAME/KEY: misc_feature
<222> LOCATION: (9)..(10)
<223> OTHER INFORMATION: n is 'T' or a modified dU in which 5-position
        is substituted with benzyl, naphthyl, pyrrolebenzyl, and/or
        tryptophan
<220> FEATURE:
<221> NAME/KEY: misc_feature
<222> LOCATION: (13)..(15)
<223> OTHER INFORMATION: n is 'T' or a modified dU in which 5-position
        is substituted with benzyl, naphthyl, pyrrolebenzyl, and/or
        tryptophan
<220> FEATURE:
<221> NAME/KEY: misc_feature
<222> LOCATION: (22)
<223> OTHER INFORMATION: n is 'T' or a modified dU in which 5-position
        is substituted with benzyl, naphthyl, pyrrolebenzyl, and/or
        tryptophan
<220> FEATURE:
<221> NAME/KEY: misc_feature
<222> LOCATION: (24)..(25)
<223> OTHER INFORMATION: n is 'T' or a modified dU in which 5-position
        is substituted with benzyl, naphthyl, pyrrolebenzyl, and/or
        tryptophan
<220> FEATURE:
<221> NAME/KEY: misc_feature
<222> LOCATION: (27)..(29)
<223> OTHER INFORMATION: n is 'T' or a modified dU in which 5-position
        is substituted with benzyl, naphthyl, pyrrolebenzyl, and/or
        tryptophan
<220> FEATURE:
<221> NAME/KEY: misc_feature
<222> LOCATION: (32)
<223> OTHER INFORMATION: n is 'T' or a modified dU in which 5-position
        is substituted with benzyl, naphthyl, pyrrolebenzyl, and/or
        tryptophan
<220> FEATURE:
<221> NAME/KEY: misc_feature
<222> LOCATION: (34)

```
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (38)
<223> OTHER INFORMATION: n is 'T' or a modified dU in which 5-position
      is substituted with benzyl, naphthyl, pyrrolebenzyl, and/or
      tryptophan

<400> SEQUENCE: 33
ncnggnccnn ccnnngacga cnanngnnng gnancganca ac                        42

<210> SEQ ID NO 34
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)..(9)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (12)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (19)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (23)..(26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (32)..(33)
<223> OTHER INFORMATION: n is 'T' or a modified dU in which 5-position
      is substituted with benzyl, naphthyl, pyrrolebenzyl, and/or
      tryptophan

<400> SEQUENCE: 34
ncaacnnnng gngccnggng gcnnnnaccg anngcgcacg c                         41

<210> SEQ ID NO 35
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
```

-continued

```
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)..(9)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (12)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)..(16)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (19)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (24)..(26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (32)..(33)
<223> OTHER INFORMATION: n is 'T' or a modified dU in which 5-position
      is substituted with benzyl, naphthyl, pyrrolebenzyl, and/or
      tryptophan

<400> SEQUENCE: 35
ncaacnnnng gngcnnggng gccnnnaccg anngcgcacg c                          41

<210> SEQ ID NO 36
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (8)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (13)..(15)
<223> OTHER INFORMATION: n is 'T' or a modified dU in which 5-position
      is substituted with benzyl, naphthyl, pyrrolebenzyl, and/or
```

```
        tryptophan
<220> FEATURE:
<221> NAME/KEY: misc_feature
<222> LOCATION: (19)..(21)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (23)..(24)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (32)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (38)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (40)
<223> OTHER INFORMATION: n is 'T' or a modified dU in which 5-position
      is substituted with benzyl, naphthyl, pyrrolebenzyl, and/or
      tryptophan

<400> SEQUENCE: 36
ncgacnancg agnnncaann nannccccca cncacaancn c                          41

<210> SEQ ID NO 37
<211> LENGTH: 50
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (5)..(6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (12)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (18)..(19)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (26)
<223> OTHER INFORMATION: n is 'T' or a modified dU in which 5-position
``` is substituted with benzyl, naphthyl, pyrrolebenzyl, and/or
tryptophan
<220> FEATURE:
<221> NAME/KEY: misc_feature
<222> LOCATION: (30)..(32)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (36)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (38)
<223> OTHER INFORMATION: n is 'T' or a modified dU in which 5-position
is substituted with benzyl, naphthyl, pyrrolebenzyl, and/or
tryptophan

<400> SEQUENCE: 37
aagcnncggn cnggnccnnc ccccncnggcn nnggcncnaa gggggccgcc                50

<210> SEQ ID NO 38
<211> LENGTH: 41
<212> TYPE: DNA
<213> ORGANISM: Artificial Sequence
<220> FEATURE:
<223> OTHER INFORMATION: core sequence of periostin aptamer, wherein n
is 'T' or a modified dU in which 5-position is substituted with
benzyl, naphthyl, pyrrolebenzyl, and/or tryptophan
<220> FEATURE:
<221> NAME/KEY: misc_feature
<222> LOCATION: (9)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (14)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (17)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (19)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (23)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (25)..(26)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (30)
<223> OTHER INFORMATION: n is 'T' or a modified dU in which 5-position
is substituted with benzyl, naphthyl, pyrrolebenzyl, and/or
tryptophan
<220> FEATURE:
<221> NAME/KEY: misc_feature
<222> LOCATION: (35)

```
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (38)..(39)
<223> OTHER INFORMATION: n is 'T' or a modified dU in which 5-position
      is substituted with benzyl, naphthyl, pyrrolebenzyl, and/or
      tryptophan

<400> SEQUENCE: 38
acaaccccnc aacngcnanc acncnnggcn caacnaanna c                           41

<210> SEQ ID NO 39
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (3)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)..(10)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (13)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (20)..(21)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (24)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
```

```
<222> LOCATION: (26)..(27)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (32)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (34)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (39)
<223> OTHER INFORMATION: n is 'T' or a modified dU in which 5-position
      is substituted with benzyl, naphthyl, pyrrolebenzyl, and/or
      tryptophann

<400> SEQUENCE: 39
ncnggnccnn ccncncnaan ngcngnngag gnancggcna c                          41

<210> SEQ ID NO 40
<211> LENGTH: 41
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (1)..(2)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (4)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (11)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)..(17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (21)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (23)
<223> OTHER INFORMATION: n is 'T' or a modified dU in which 5-position
      is substituted with benzyl, naphthyl, pyrrolebenzyl, and/or
      tryptophan
<220> FEATURE:
```

```
<221> NAME/KEY: misc_feature
<222> LOCATION: (26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (29)..(30)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (34)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (39)
<223> OTHER INFORMATION: n is 'T' or a modified dU in which 5-position
      is substituted with benzyl, naphthyl, pyrrolebenzyl, and/or
      tryptophan

<400> SEQUENCE: 40
nngncgcang ngcggnncag ncnggnccnn cagnaccgna c                         41

<210> SEQ ID NO 41
<211> LENGTH: 52
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (8)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (11)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (14)..(15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (18)..(20)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (27)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (29)..(30)
<223> OTHER INFORMATION: n is 'T' or a modified dU in which 5-position
      is substituted with benzyl, naphthyl, pyrrolebenzyl, and/or
      tryptophan
```

```
<220> FEATURE:
<221> NAME/KEY: misc_feature
<222> LOCATION: (32)..(34)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (37)
<223> OTHER INFORMATION: n is 'T' or a modified dU in which 5-position
      is substituted with benzyl, naphthyl, pyrrolebenzyl, and/or
      tryptophann
<220> FEATURE:
<221> NAME/KEY: misc_feature
<222> LOCATION: (39)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (43)
<223> OTHER INFORMATION: n is 'T' or a modified dU in which 5-position
      is substituted with benzyl, naphthyl, pyrrolebenzyl, and/or
      tryptophan

<400> SEQUENCE: 41
acgagncngg nccnnccnnn gacgacnann gnnnggnanc gancaacaac aa            52

<210> SEQ ID NO 42
<211> LENGTH: 51
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (13)..(14)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (17)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (21)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (25)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (28)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (31)..(32)
<223> OTHER INFORMATION: n is 'T' or a modified dU in which 5-position
      is substituted with benzyl, naphthyl, pyrrolebenzyl, and/or
``` tryptophan
<220> FEATURE:
<221> NAME/KEY: misc_feature
<222> LOCATION: (41)
<223> OTHER INFORMATION: n is 'T' or a modified dU in which 5-position
      is substituted with benzyl, naphthyl, pyrrolebenzyl, and/or
      tryptophann

<400> SEQUENCE: 42
acgagncaca cgnngangac ngganggnag nnaaagaggg ngggggcaaca a     51

<210> SEQ ID NO 43
<211> LENGTH: 51
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (6)..(7)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (9)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (14)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (16)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (21)..(22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (28)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (31)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (34)..(35)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (44)
<223> OTHER INFORMATION: n is 'T' or a modified dU in which 5-position is substituted with benzyl, naphthyl, pyrrolebenzyl, and/or
      tryptophan

<400> SEQUENCE: 43
acgagnngnc gcangngcgg nncagncngg nccnncagca ccgnacaaca a         51

<210> SEQ ID NO 44
<211> LENGTH: 51
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (8)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (11)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (14)..(15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (18)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (22)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (25)..(26)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (29)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (31)..(32)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (37)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (39)

```
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (44)
<223> OTHER INFORMATION: n is 'T' or a modified dU in which 5-position
      is substituted with benzyl, naphthyl, pyrrolebenzyl, and/or
      tryptophan

<400> SEQUENCE: 44
acgagncngg nccnnccncc cnaanngcng nngaggnanc ggcnacaaca a        51

<210> SEQ ID NO 45
<211> LENGTH: 11
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (6)
<223> OTHER INFORMATION: n is 'T' or a modified dU in which 5-position
      is substituted with benzyl, naphthyl, pyrrolebenzyl, and/or
      tryptophan

<400> SEQUENCE: 45
acgagnaaca a                                                    11

<210> SEQ ID NO 46
<211> LENGTH: 40
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (20)
<223> OTHER INFORMATION: n is 'T' or a modified dU in which 5-position
      is substituted with benzyl, naphthyl, pyrrolebenzyl, and/or
      tryptophan

<400> SEQUENCE: 46
gatgtgagtg tgtgacgagn aacaacagaa caaggaaagg                     40

<210> SEQ ID NO 47
<211> LENGTH: 60
<212> TYPE: DNA
<213> ORGANISM: Artificial Sequence
<220> FEATURE:
<223> OTHER INFORMATION: core sequence of periostin aptamer, wherein n
      is 'T' or a modified dU in which 5-position is substituted with
      benzyl, naphthyl, pyrrolebenzyl, and/or tryptophan
<220> FEATURE:
<221> NAME/KEY: misc_feature
<222> LOCATION: (21)..(60)
<223> OTHER INFORMATION: n is 'T' or a modified dU in which 5-position
      is substituted with benzyl, naphthyl, pyrrolebenzyl, and/or
      tryptophan

<400> SEQUENCE: 47
cctttccttg ttctgttgtt nnnnnnnnnn nnnnnnnnnn nnnnnnnnnn nnnnnnnnnn 60

<210> SEQ ID NO 48
<211> LENGTH: 19
<212> TYPE: DNA
<213> ORGANISM: Artificial Sequence
```

```
<220> FEATURE:
<223> OTHER INFORMATION: 5' primer

<400> SEQUENCE: 48
gatgtgagtg tgtgacgag                                                    19

<210> SEQ ID NO 49
<211> LENGTH: 20
<212> TYPE: DNA
<213> ORGANISM: Artificial Sequence
<220> FEATURE:
<223> OTHER INFORMATION: 3' primer

<400> SEQUENCE: 49
cctttccttg ttctgttgtt                                                   20

<210> SEQ ID NO 50
<211> LENGTH: 17
<212> TYPE: DNA
<213> ORGANISM: Artificial Sequence
<220> FEATURE:
<223> OTHER INFORMATION: M13 primer

<400> SEQUENCE: 50
caggaaacag ctatgac                                                      17

<210> SEQ ID NO 51
<211> LENGTH: 51
<212> TYPE: DNA
<213> ORGANISM: Artificial Sequence
<220> FEATURE:
<223> OTHER INFORMATION: control aptamer
<220> FEATURE:
<221> NAME/KEY: misc_feature
<222> LOCATION: (7)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (12)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (15)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (28)
<223> OTHER INFORMATION: n is 'T' or a modified dU in which 5-position
      is substituted with benzyl, naphthyl, pyrrolebenzyl, and/or
      tryptophan
<220> FEATURE:
<221> NAME/KEY: misc_feature
<222> LOCATION: (39)
<223> OTHER INFORMATION: n is 'T' or a modified dU in which 5-position
      is substituted with benzyl, naphthyl, pyrrolebenzyl, and/or
      tryptophan

<400> SEQUENCE: 51
acgaggnacg gngcngaagg accagacnga accgcacang cgacaaaaca a                51
```

The invention claimed is:

1. A periostin aptamer that specifically binds to periostin and is in a length of 25 to 100 bases comprising 5 to 20 modified bases that are substituted with a hydrophobic functional group selected from the group consisting of a naphthyl group, a benzyl group, a pyrrole benzyl group, and tryptophan at 5-position of dU (deoxyuracil), wherein the nucleotide sequence of the periostin aptamer is selected from the group consisting of SEQ ID NO: 5 to SEQ ID NO: 40, where n in the nucleotide sequence is a modified base substituted at 5-position of dU (deoxyuracil) with a hydrophobic functional group selected from the group consisting of a naphthyl group, a benzyl group, a pyrrole benzyl group, and tryptophan.

2. The periostin aptamer according to claim 1, wherein the periostin aptamer further comprises an additional nucleotide sequence at the 5'-terminal, 3'-terminal or both terminals selected from the group consisting of SEQ ID NO: 1 to SEQ ID NO: 4.

3. The periostin aptamer according to claim 2, wherein the periostin aptamer is represented by the following nucleotide sequence of SEQ ID NO: 45 or SEQ ID NO: 46:

```
                                            (SEQ ID NO: 45)
5'-ACGAG-[N]-AACAA-3'
or
                                            (SEQ ID NO: 46)
5'-GATGTGAGTGTGTGACGAG-[N]-AACAACAGAACAAGGAAAGG-3',
``` in the nucleotide sequence, 'N' consists of 25 to 80 bases, each base is independently selected from the group consisting of A, C, G, deoxy forms of A, C, and G, and a modified base that is substituted at 5-position of dU (deoxyuracil) with a naphthyl group, a benzyl group, a pyrrole benzyl group, and tryptophan, and the number of modified base is 5 to 20.

4. The periostin aptamer according to claim 3, wherein the 'N' is a nucleotide sequence selected from the group consisting of SEQ ID NO: 5 to SEQ ID NO: 40.

5. The periostin aptamer according to claim 4, wherein the periostin aptamer is represented by the nucleotide sequence selected from the group consisting of SEQ ID NO: 41 to SEQ ID NO: 44.

6. The periostin aptamer according to claim 1, wherein the periostin aptamer comprises an additional nucleotide sequence consisting of 3 to 25 bases at 5'-terminal, 3'-terminal, or both terminals, and consists of total 30 to 120 bases.

7. The periostin aptamer according to claim 1, wherein the periostin aptamer is modified by binding of at least one selected from the group consisting of PEG (polyethylene glycol), idT (inverted deoxythymidine), LNA (Locked Nucleic Acid), 2'-methoxy nucleoside, 2'-amino nucleoside, 2'F-nucleoside, amine linker, thiol linker and cholesterol, to the 5'-terminal, 3'-terminal, or both terminals of the periostin aptamer.

8. A pharmaceutical composition comprising the periostin aptamer of claim 1 as an active ingredient.

9. The pharmaceutical composition according to claim 8, wherein the periostin aptamer is modified by binding of at least one selected from the group consisting of PEG (polyethylene glycol), idT (inverted deoxythymidine), LNA (Locked Nucleic Acid), 2'-methoxy nucleoside, 2'-amino nucleoside, 2'F-nucleoside, amine linker, thiol linker and cholesterol, to the 5'-terminal, 3'-terminal, or both terminals of the periostin aptamer.

10. A method for treating cancer or inhibiting cancer metastasis, comprising administering a pharmaceutically effective amount of the periostin aptamer of claim 1 to a subject in need of treatment of cancer or inhibition of cancer metastasis.

11. The method according to claim 10, wherein the periostin aptamer is modified by binding of at least one selected from the group consisting of PEG (polyethylene glycol), idT (inverted deoxythymidine), LNA (Locked Nucleic Acid), 2'-methoxy nucleoside, 2'-amino nucleoside, 2'F-nucleoside, amine linker, thiol linker and cholesterol, to the 5'-terminal, 3'-terminal, or both terminals of the periostin aptamer.

12. The method according to claim 10, wherein the cancer is at least one selected from the group consisting of breast cancer, colorectal cancer, lung cancer, gallbladder cancer, pancreatic cancer, stomach cancer, uterine cancer, head and neck squamous cell carcinoma, prostate cancer, and glioblastoma.

* * * * *